US012653457B2

(12) United States Patent
Moussavi et al.

(10) Patent No.: US 12,653,457 B2
(45) Date of Patent: Jun. 16, 2026

(54) SYSTEM AND METHODS FOR SCREENING OBSTRUCTIVE SLEEP APNEA DURING WAKEFULNESS USING ANTHROPOMETRIC INFORMATION AND TRACHEAL BREATHING SOUNDS

(71) Applicant: University of Manitoba, Winnipeg (CA)

(72) Inventors: Zahra Moussavi, Winnipeg (CA); Ahmed Elwali, Winnipeg (CA)

(73) Assignee: University of Manitoba, Winnipeg (CA)

( * ) Notice: Subject to any disclaimer, the term of this patent is extended or adjusted under 35 U.S.C. 154(b) by 942 days.

(21) Appl. No.: 17/349,298

(22) Filed: Jun. 16, 2021

(65) Prior Publication Data

US 2021/0401364 A1      Dec. 30, 2021

Related U.S. Application Data

(60) Provisional application No. 63/040,714, filed on Jun. 18, 2020.

(51) Int. Cl.
A61B 5/00 (2006.01)
G16H 50/70 (2018.01)

(52) U.S. Cl.
CPC .......... A61B 5/4818 (2013.01); A61B 5/7267 (2013.01); A61B 5/7275 (2013.01); G16H 50/70 (2018.01)

(58) Field of Classification Search
CPC .... A61B 5/4818; A61B 5/7267; G16H 50/70; G16H 50/20; G16H 50/30; G16H 15/00; G16H 40/63; G16H 50/50; G16H 40/60

USPC .............. 703/11; 705/2, 3; 706/46; 600/529
See application file for complete search history.

(56) References Cited

U.S. PATENT DOCUMENTS

| | | | | |
|---|---|---|---|---|
| 6,839,581 B1 * | 1/2005 | El-Solh | .................. | A61B 5/145 |
| | | | | 600/323 |
| 11,676,719 B2 * | 6/2023 | Feczko | .................. | G16H 20/70 |
| | | | | 706/12 |
| 2014/0142452 A1 | 5/2014 | Moussavi et al. | | |
| 2014/0330095 A1 * | 11/2014 | Kazem-Moussavi | ........................ | |
| | | | | A61B 5/742 |
| | | | | 600/301 |
| 2018/0121626 A1 * | 5/2018 | Abedini | ................. | G16H 50/30 |
| 2018/0353126 A1 * | 12/2018 | Gozal | ................ | A61B 5/14551 |
| 2019/0298271 A1 | 10/2019 | Zigel et al. | | |
| 2019/0328457 A1 * | 10/2019 | Villongco | .............. | G16H 40/67 |
| 2020/0185102 A1 * | 6/2020 | Leventhal | ............. | G06F 40/117 |
| 2020/0229736 A1 * | 7/2020 | Saporito | ................. | G06F 3/011 |

(Continued)

FOREIGN PATENT DOCUMENTS

| | | |
|---|---|---|
| CN | 102138795 | 8/2011 |
| CN | 112089413 | 12/2020 |

*Primary Examiner* — Jacqueline Cheng
*Assistant Examiner* — Jonathan E. Cooper
(74) *Attorney, Agent, or Firm* — Kyle R Satterthwaite; Ryan W Dupuis; Ade & Company Inc.

(57) ABSTRACT

Novel systems and methods use extracted features from audio signals of patient breathing sounds taken during periods of full wakefulness in order to classify patients as either having, or not having, obstructive sleep apnea using a Random Forest machine learning algorithm. In some embodiments, the features are preprocessed then modeled. The models with a high correlation to the response and low overlap percentages are selected for use in the Random Forest classification process.

20 Claims, 14 Drawing Sheets

(56)　　　　　References Cited

U.S. PATENT DOCUMENTS

| | | | |
|---|---|---|---|
| 2020/0375549 A1* | 12/2020 | Wexler | G16H 50/20 |
| 2021/0030353 A1* | 2/2021 | Groenendaal | G06N 20/20 |
| 2023/0043406 A1* | 2/2023 | Zhang | G06N 5/01 |

* cited by examiner

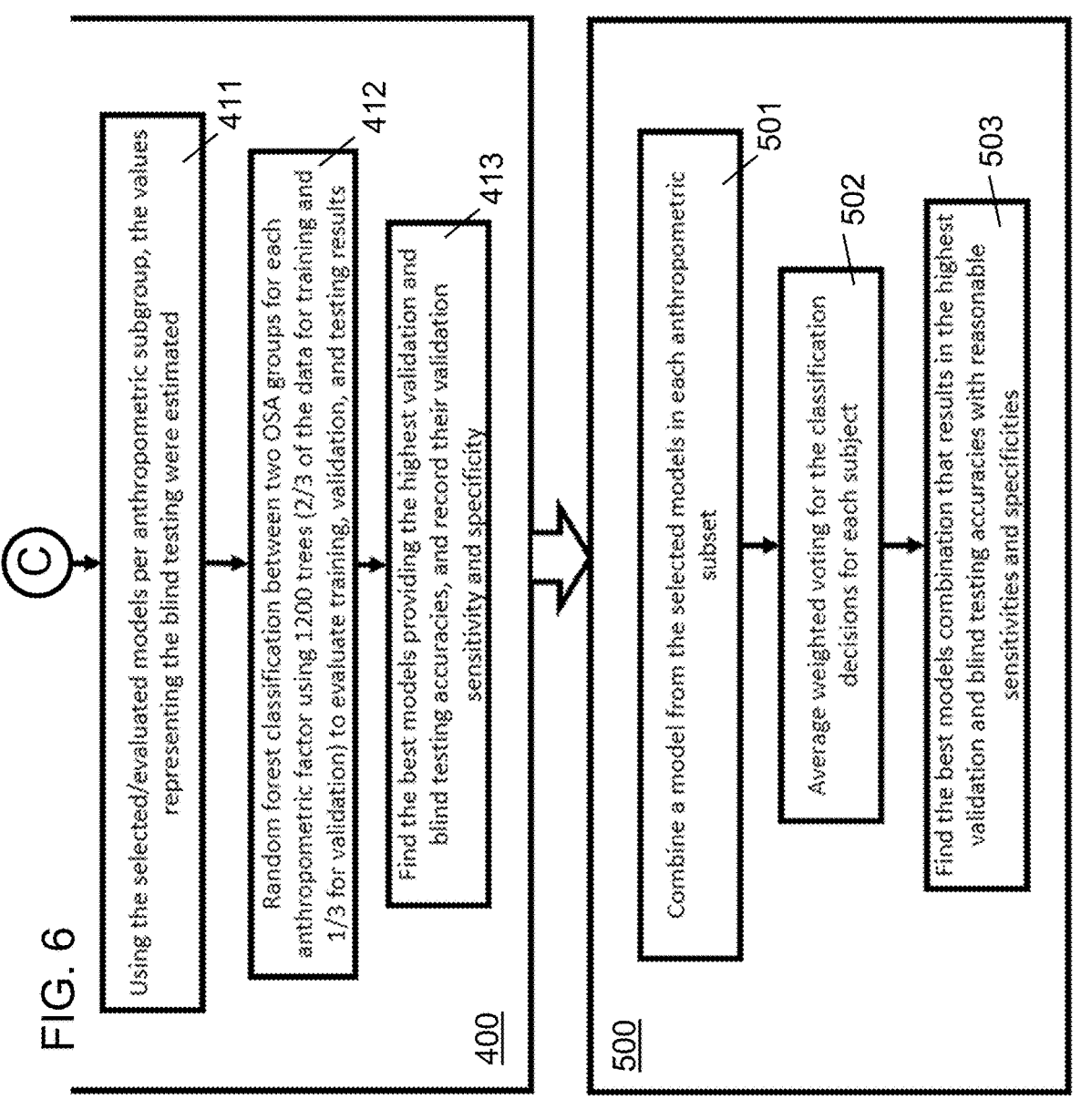

411 — Using the selected/evaluated models per anthropometric subgroup, the values representing the blind testing were estimated 412 — Random forest classification between two OSA groups for each anthropometric factor using 1200 trees (2/3 of the data for training and 1/3 for validation) to evaluate training, validation, and testing results 413 — Find the best models providing the highest validation and blind testing accuracies, and record their validation sensitivity and specificity

400

501 — Combine a model from the selected models in each anthropometric subset

502 — Average weighted voting for the classification decisions for each subject

503 — Find the best models combination that results in the highest validation and blind testing accuracies with reasonable sensitivities and specificities

500

New Modified AWakeOSA (patient testing)

FIG. 15
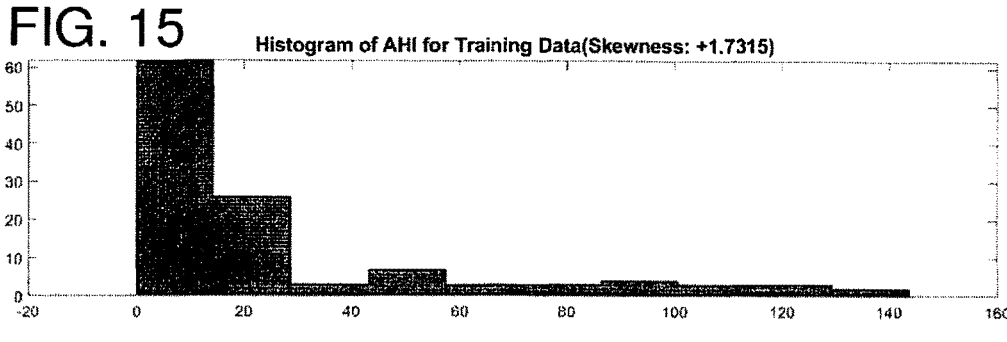
Histogram of AHI for Training Data(Skewness: +1.7315)
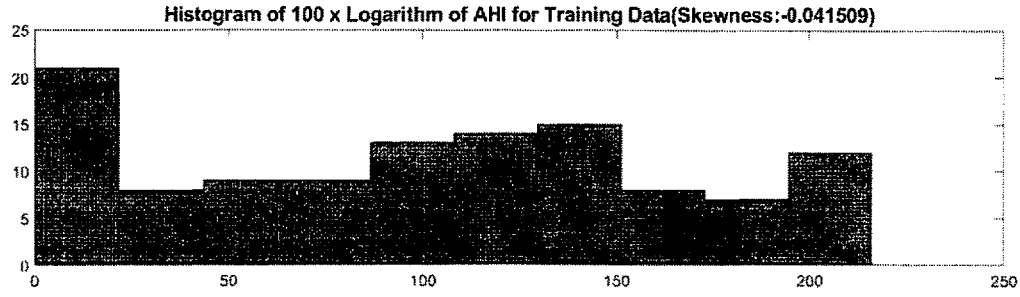
Histogram of 100 x Logarithm of AHI for Training Data(Skewness:-0.041509)
FIG. 16A
FIG. 16B
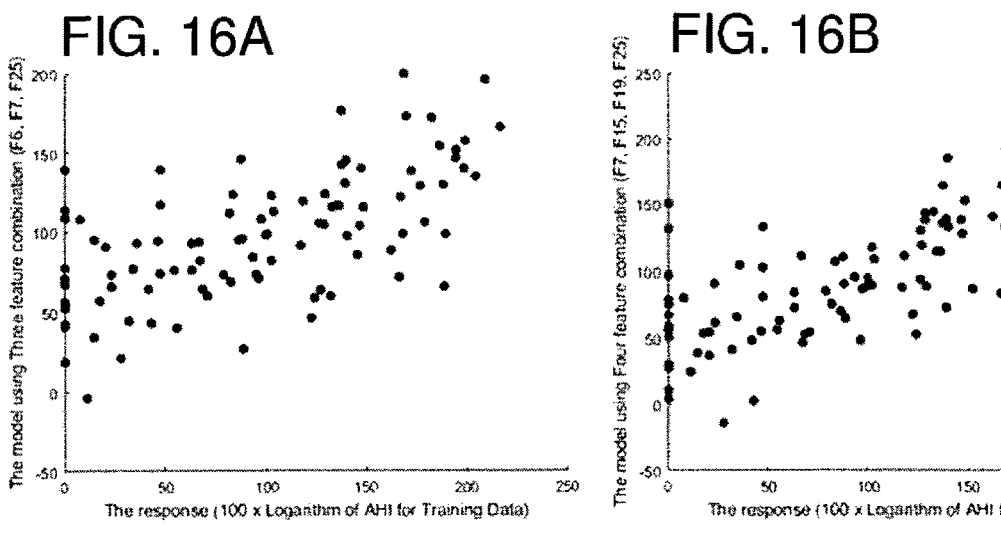
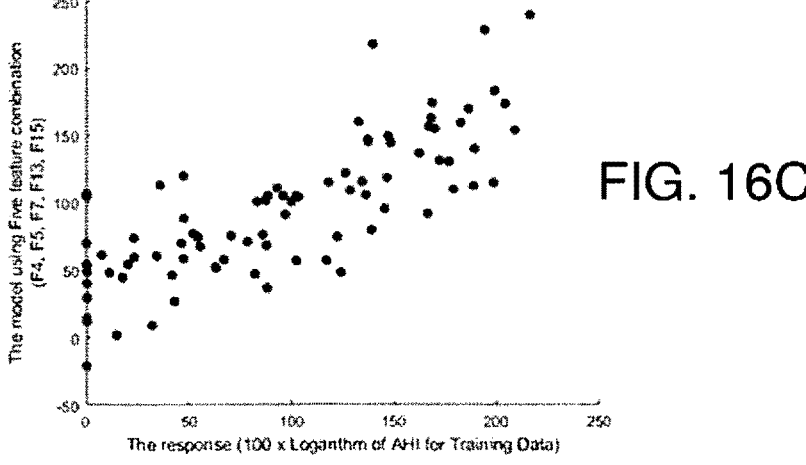
FIG. 16C

SYSTEM AND METHODS FOR SCREENING OBSTRUCTIVE SLEEP APNEA DURING WAKEFULNESS USING ANTHROPOMETRIC INFORMATION AND TRACHEAL BREATHING SOUNDS

CROSS-REFERENCE TO RELATED APPLICATIONS

This application claims domestic priority benefit under 35 U.S.C. 119(e) of U.S. Provisional Patent Application No. 63/040,714, filed Jun. 18, 2020, and foreign priority benefit under 35 U.S.C. 119(a) of Canadian Patent Application No. 3,089,395, both of which are incorporated herein by reference in their entirety.

FIELD OF THE INVENTION

The present invention relates to computer-implemented systems and methods employing machine learning to classifying patients as either having, or not having, obstructive sleep apnea based on recorded audio of the patient's breathing sounds, and more particularly based on breathing sounds taken during periods of full wakefulness.

BACKGROUND

Obstructive sleep apnea (OSA) is a common syndrome characterized by repetitive episodes of complete (apnea) or partial (hypopnea) pharyngeal collapse during sleep (American Academy of Sleep Medicine, 2005). The severity of OSA is commonly measured by the apnea/hypopnea index (AHI), which is the number of apnea/hypopnea episodes per hour of sleep. Usually, an AHI<5 is considered as non-OSA, 5<AHI<15 as mild, 15<AHI<30 as moderate and AHI>30 as severe OSA. Clinically, however, it is a common practice to consider individuals with AHI<15 as those who may not benefit from treatment, and therefore an AHI of 15 is used as a threshold to determine severity (Littner, 2007; Medscape, Aug. 23, 2016). Signs and symptoms of OSA include excessive daytime sleepiness, loud snoring, and observed episodes of breathing ceasing, gasping and/or choking during sleep (Epstein et al., 2009). OSA can severely impact the quality of sleep, and therefore the quality of life. It is associated with an increased risk of developing cardiovascular problems, hypertension, stroke, depression, diabetes, and headaches, as well as traffic accidents (ResMed, 2013). These comorbidities may be worsened if OSA is not treated (Bonsignore et al., 2019). In addition, it has been suggested to consider the existence of critical comorbidity for OSA to determine its severity and its treatment management (Vavougios, Natsios, Pastaka, Zarogiannis, & Gourgoulianis, 2016). Furthermore, not taking suitable precautions (due to lack of accurate and reliable screening tools for OSA) prior to full anesthesia of OSA patients undergoing a sugary may lead to perioperative morbidity and mortality (American Society of Anesthesiologists, 2006; Gross et al., 2014). An accurate OSA screening tool, in particular for patients prior to undergoing a surgery requiring full anesthesia, would reduce these risks (American Society of Anesthesiologists, 2006; Gross et al., 2014). This paper reports on a novel OSA classification procedure as a quick and accurate screening tool, based on anthropometric information and a few minutes of breathing sounds recorded during wakefulness.

The gold standard for OSA diagnosis is an overnight Polysomnography (PSG) assessment. However, it is costly and time-consuming. There are many portable monitoring devices for OSA, but they all require an overnight recording. In Canada and US, about 10% of the population suffer from OSA (Young, T. et al., 2008), while the number of qualified sleep rooms available for conducting PSG studies is limited. Consequently, there is a long waiting list of patients; in some places, the waiting time exceeds a year for an overnight full PSG. Due to the mentioned facts, it is very desirable for anesthesiologists, in particular, to have an efficient perioperative management plan based on an objective, reliable and prompt diagnostic or screening tool for OSA (American Society of Anesthesiologists, 2006; Chung & Elsaid, 2009; Gross et al., 2014).

A quick OSA screening tool that is commonly used for patients undergoing surgery requiring full anesthesia is the STOP-BANG questionnaire (Nagappa et al., 2015). It is a simple, quick, and inexpensive assessment that is reported to have a high sensitivity (~93%) but at the cost of a very poor specificity (~36%) (Nagappa et al., 2015). Any assessment with poor specificity indirectly increases the referral rate to the full PSG study; thus, increases healthcare system's cost. Therefore, there is a need for a quick and reliable objective technology with high sensitivity and specificity for OSA screening applicable during wakefulness.

The use of tracheal breathing sound analysis during wakefulness has also been proposed for screening OSA (Elwali & Moussavi, 2017; Karimi, 2012; Montazeri et al., 2012; Moussavi, Z. et al., 2015). Several research groups around the globe have been working on the possibility of using either tracheal breathing or vocal sounds during wakefulness to predict OSA (Goldshtein et al., 2011; Jung et al., 2004; Kriboy et al., 2014; Sola-Soler et al., 2014). Overall, those studies have reported an accuracy between 79.8% to 90% with both comparable sensitivity and specificity. While their accuracy is much better than the STOP-BANG questionnaire, none of the reported accuracies indicate blind test accuracy. In addition, their unbalanced sample sizes were quite small [23 (minimum 10 subjects for non-OSA) and 70 (minimum 13 subjects for OSA)] given the heterogeneity of OSA population.

Accordingly, there is a need for improved techniques and technology relating to the use of fully-awake tracheal breathing sound analysis for OSA patient screening.

SUMMARY OF THE INVENTION

According to a first aspect of the invention, there is provided a method of deriving an obstructive sleep apnea (OSA) screening tool, said method comprising:
  (a) obtaining an initial dataset that comprises, for each of a plurality of human test subjects from whom respective audio recordings were taken during periods of full wakefulness, a respective subject dataset in which there is stored at least:
   a known OSA severity parameter of the test subject;
   anthropometric data identifying different anthropometric parameters of the test subject; and
   audio data containing stored audio signals from said respective audio recording of said test subject;
  (b) extracting at least spectral and bi-spectral features from the audio data of the subject datasets;
  (c) selecting a training dataset from said initial dataset, and from said training dataset, grouping together the subject datasets from a first high-severity group of said test subjects whose known OSA seventy parameters are above a first threshold, and grouping together the subject datasets of a second low-severity group of said test subjects whose known OSA severity parameters are below a second threshold that is lesser than said first threshold;

(d) based on the anthropometric data, dividing the subject datasets from each of the high-severity and low-severity groups into a plurality of anthropometrically distinct subsets;

(e) deriving input for a classifier training procedure at least partly by, for each anthropometrically distinct subset, filtering said extracted features down to a selected subset of features;

(f) using said derived input to train a classifier for the purpose of classifying a human patient as either OSA or non-OSA based on a respective patient dataset that contains at least:

anthropometric data identifying different anthropometric parameters of the patient; and at least one of either:

audio data containing stored audio signals from a respective audio recording of said patient during a period of full wakefulness; and/or feature data concerning features already extracted from said audio signals from the respective audio recording of said patient.

According to a second aspect of the invention, there is provided a method of performing an obstructive sleep apnea (OSA) screening test on a patient, said method comprising:

(a) obtaining one or more computer readable media on which there is stored:

a trained classifier derived in the manner recited in steps (a) through (f) of the first aspect of the invention;

for said patient, a patient dataset of the type recited in step (f) of the first aspect of the invention; and statements and instructions executable by one or more computer processors;

(b) through execution of said statements and instructions by said one or more computer processors:

(i) reading the anthropometric data of said patient dataset;

(ii) running the trained classifier multiple times, each time starting with input composed of or derived from a different combination of pertinent features, comprised of at least spectral and bi-spectral features, particularly selected or derived from the patient dataset for a different anthropometric parameter read from the anthropometric data of said patient dataset, and for each run of said trained classifier, deriving therefrom a respective classification result classifying the patient as either OSA or non-OSA;

(iii) based on the classification results from step (b)(ii), deriving a final classification result for the patient; and (iv) storing or displaying said final classification.

According to a third aspect of the invention, there is provided a method of performing an obstructive sleep apnea (OSA) screening test on a patient, said method comprising:

(a) obtaining one or more computer readable media on which there is stored:

a trained classifier for classifying said patient as either OSA or non-OSA;

for said patient, a patient dataset of the type recited in step (f) of the first aspect of the invention; and statements and instructions executable by one or more computer processors;

(b) through execution of said statements and instructions by said one or more computer processors:

(i) reading the anthropometric data of said patient dataset;

(ii) running the trained classifier multiple times, each time starting with input composed of or derived from a different combination of pertinent features, comprised at least of spectral and bi-spectral features, particularly selected or derived from the patient dataset for a different anthropometric parameter read from the anthropometric data of said patient dataset, and for each run of said trained classifier, deriving therefrom a respective classification result classifying the patient as either OSA or non-OSA;

(iii) based on the classification results from step (b)(ii), deriving a final classification result for the patient; and (iv) storing or displaying said final classification.

According to a fourth aspect of the invention, there is provided one or more non-transitory computer readable media having stored thereon executable statements and instructions for performing step (b) of the second or third aspect of the invention.

According to a fifth aspect of the invention, there is provided a system for deriving or operating an obstructive sleep apnea screening tool, said system comprising one or more computers comprising one or more computer processors, one or more non-transitory computer readable media connected thereto, and a microphone connected to one of said one or more computers for capturing respective audio recordings of breathing cycles of human test subjects and/or patients during periods of full wakefulness and storing said audio recordings as audio data on said one or more non-transitory computer readable media, wherein said one or more non-transitory computer readable media also have stored thereon executable statements and instructions configured to, when executed by the one or more processors, extract features from said audio recordings, and perform steps (a) through (f) of the first aspect of the invention, and/or step (b) the second or third aspect of the invention.

BRIEF DESCRIPTION OF THE DRAWINGS

Preferred embodiments of the invention will now be described in conjunction with the accompanying drawings in which:

FIG. 6 is a flowchart sequence illustrating a remainder of the fourth stage of the subject data collection and classifier training process, and a subsequent fifth model-combination stage thereof.

FIG. 15 shows, from a second experiment employing the full subject data collection and classifier training process of FIGS. 3 to 6, a histogram of the AHI response before and after scaling thereof.

FIG. 16 shows, from the second experiment, scatter plots between the response and the predicted response using models of three, four, and five features.

DETAILED DESCRIPTION

Systems & Processes

Disclosed herein are the details of systems and processes employing a novel and inventive decision-making algorithm, called AWakeOSA, that uses anthropometric information and a few minutes of tracheal breathing sounds recorded during wakefulness to identify OSA individuals in need of treatment. This algorithm considers the confounding anthropometric effects on the breathing sounds and uses them to predict the severity of OSA in a subgroup with a similar confounding variable.

Figures 1, 2:
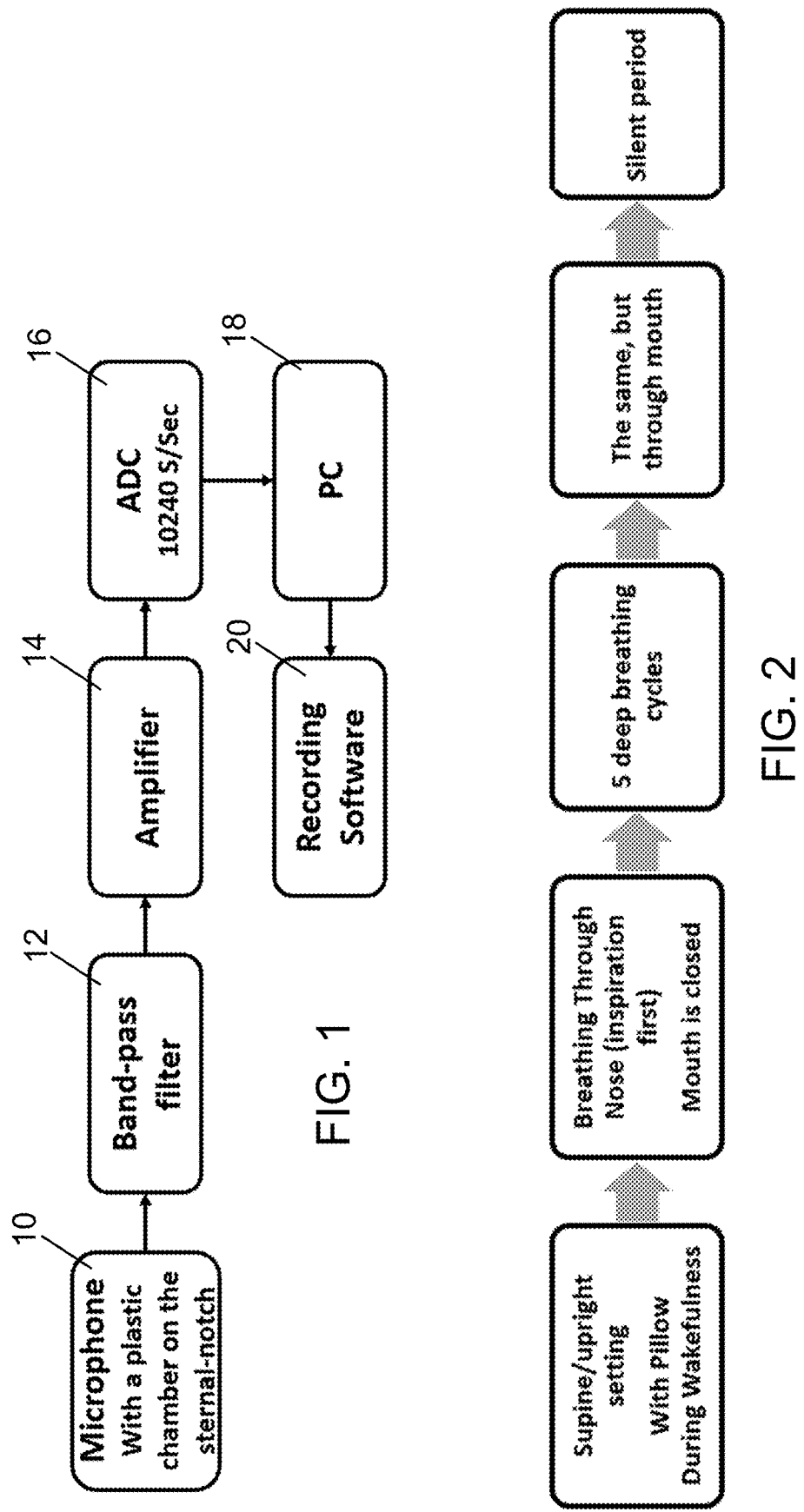
FIG. 1 is a schematic block diagram of a system of the present invention usable to both build and subsequently execute a computerized screening tool for classifying patients as either having or not having obstructive sleep apnea (OSA or non-OSA).
FIG. 2 schematically illustrates a recording procedure for recording tracheal breathing sounds during periods of full wakefulness, both from test subjects whose results are used as training and blind testing data to build the screening tool, and from patients who are subsequently screened using said screening tool.

Referring to FIG. 1, tracheal breathing sounds are recorded, preferably using a flat-response wide-frequency range microphone 10 inserted into a plastic microphone coupler delimiting a conically-shaped air chamber between the microphone and skin (FIG. 1), for example measuring approximately 2-mm deep. The microphone 10 is placed over suprasternal notch of the trachea and held in such position, for example using a double-sided adhesive ring tape. The acoustic signals are routed through a band-pass filter 12 and amplifier 14, and converted to a digital signal by an analog to digital converter 16 to enable digital recording of the audio by a computer 18 executing suitable recording software 20, so as to store the digital audio data in computer readable memory.

Referring to FIG. 2, the audio recordings are separately made in supine and upright positions of subjects and patients both with and without the subject's/patient's head resting on a pillow. Subjects/patients are instructed to breathe multiple (>2) full deep breathing cycles through their nose with their mouth closed, followed by multiple deep breaths through their mouth while wearing a nose clip. The recording is followed or started with recording a silent period. All recordings are started with an inspiration phase and marked by the voice of an operator conducting the recording procedure, or by another audible marker clearly distinguishable from recorded breathing sounds. This same recording procedure is employed both for "test subjects" whose recording are used as training data to build a computerized OSA screening tool, and for "patients" whose recordings are being used to classify those patients as either OSA or non-OSA using the trained screening tool.

Figure 3:
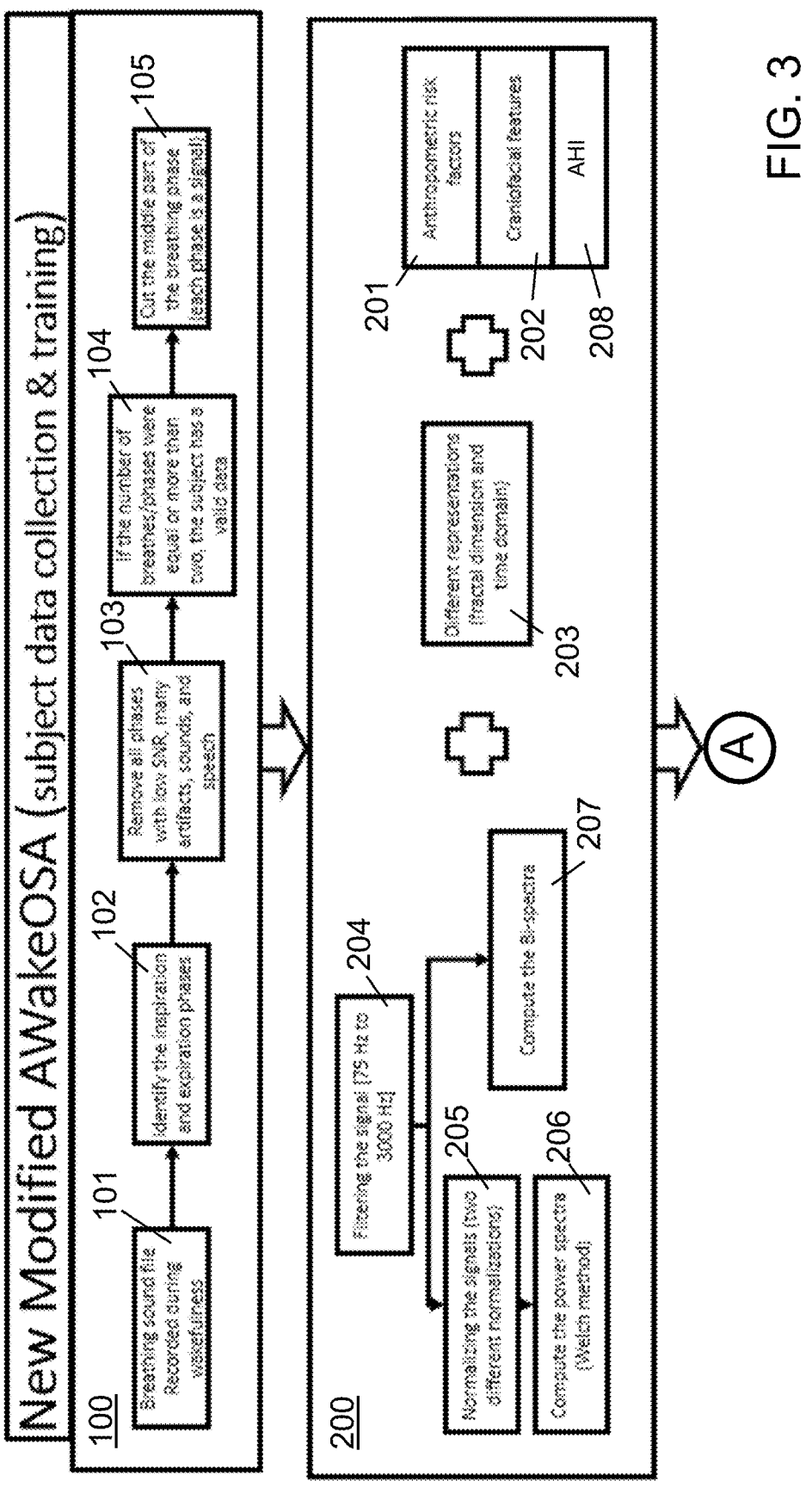
FIG. 3 is a flowchart sequence illustrating first and second data collection stages of a subject data collection and classifier training process for building said computerized screening tool.
Figure 9:
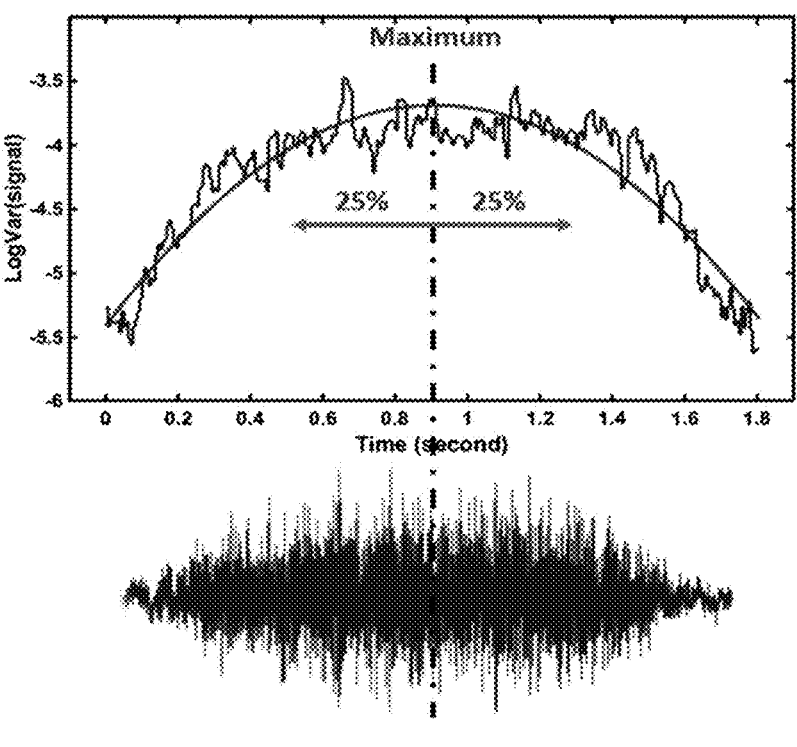
FIG. 9 shows a plot of a typical breathing inspiratory phase tracheal sound signal (the bottom graph) and its envelope roughly representing its estimated flow (the top graph) with middle period identification.

Turning to FIG. 3, first and second stages of a data collection and classifier training procedure for building said computerized OSA screening tool are shown therein. At the first step 101 of the first stage 100, the breathing sounds of a test subject are recorded using the aforementioned recording procedure of FIG. 2. Next, at step 102, from the digitally recorded breathing sound signals of each nose and mouth breathing maneuver, inspiratory and expiratory sounds are extracted and saved in separate files on the computer readable memory. Then, at step 103, all recorded signals are investigated and inspected to exclude any breathing phases or cycles that have artifacts, vocal noises, tones, interruption or low signal to noise ratio (SNR) compared to the background noise. At step 104, any signal with less than two breath cycles is excluded from the analysis. Next, at step 105, using the logarithm of the variance of each phase signal that is representative of the respiratory flow (Yadollahi, A. & Moussavi, 2007), the 50% duration around the maximum of each breathing phase is selected for further analysis, as schematically shown in FIG. 9.

Still referring to FIG. 3, in the second stage 200, information collected from each test subject is added to a datastore that is stored on a same or different computer readable memory from that on which the digital audio was recorded. This stored information includes at least anthropometric data 201 indicative of OSA risk factors (ex. BMI, age, etc.), an may also include answers to the STOP-BAND questionnaire (ex. Low/high blood pressure, snoring, etc.), and/or craniofacial measurements 202 (ex. Face width, neck width, neck depth, etc.). Different features and representations are computed using the breathing sound signals, for example including fractal dimensions and the time domain, and likewise are recorded in the datastore, as shown at 203. At step 204, each breathing sound phase is filtered individually between 75 Hz to 3000 Hz to reduce the effects of heartbeats, muscle motion, plausible 60 Hz harmonics, and background noise.

Then, at steps 205-207, the power spectrum and bi-spectrums are computed for each breathing phase followed by averaging the spectrums for one type of maneuvers (ex. Inspiratory phases recorded from the mouth) for each subject. At step 205, before computing the power spectrum, each filtered signal is normalized by its variance envelope (i.e., a smoothed version of itself using the Moving Average method of certain samples sequence) (Gavriely & Cugell, 1995), and then by its energy (standard deviation) to remove the effect of plausible airflow fluctuation between the breathing cycles. At step 206, the power spectrum is calculated using the Welch method (Proakis, 2006) with certain window size and overlapping between adjacent windows. The spectral data and bi-spectral data are recorded in the datastore in association with the stored information from the test subject. The test subjects have already undergone, or are subject to a PSG assessment from which an AHI assigned to each subject is also stored in the datastore, as shown at 208, in association with the anthropometric and craniofacial data 201, 202 and any other patient-specific information recorded for each test subject, which is collectively referred to as a subject dataset.

Figure 4:
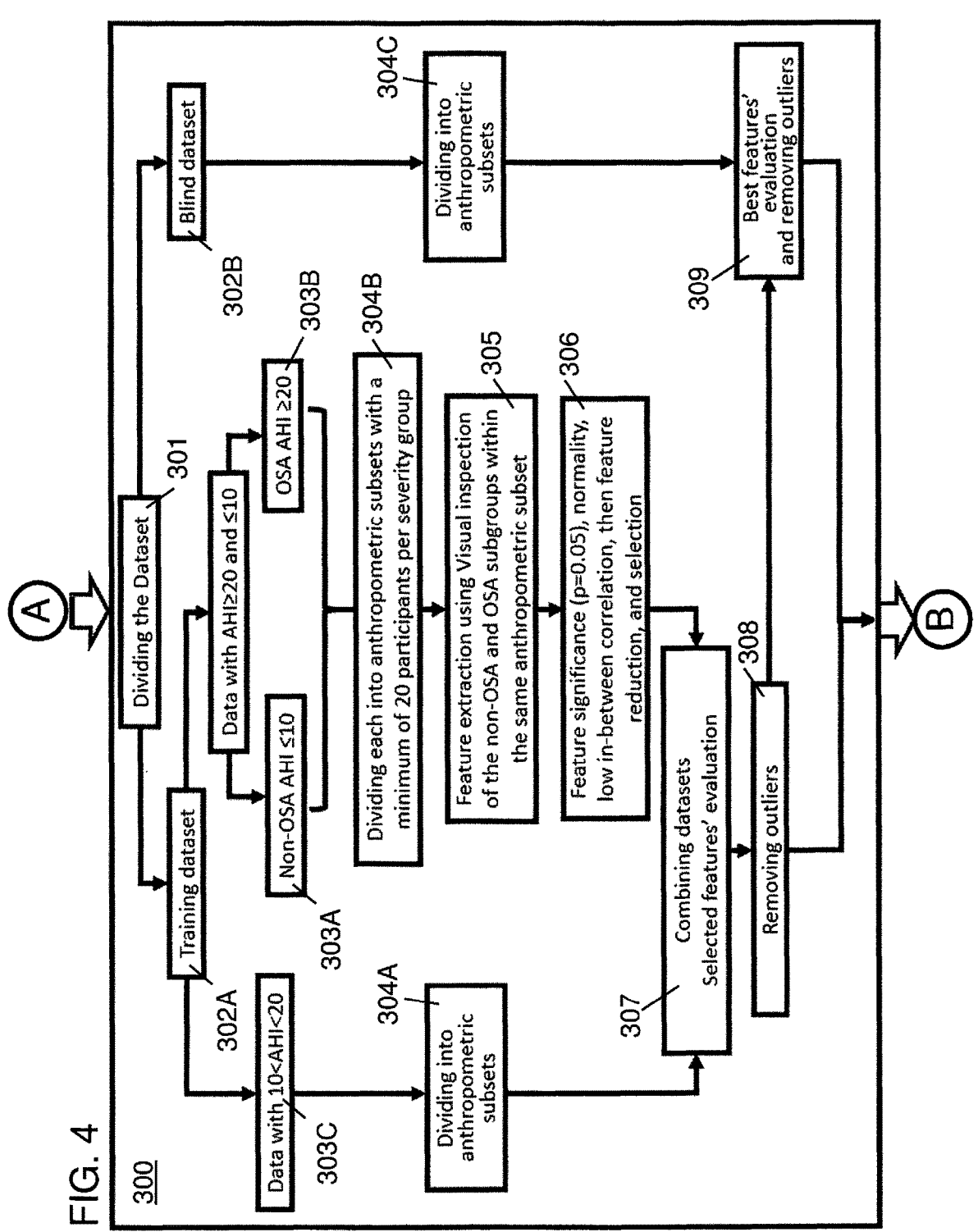
FIG. 4 is a flowchart sequence illustrating a third data processing and feature reduction/selection stage of the subject data collection and classifier training process.

The subject datasets recorded in the second stage 200 for a group of test subjects forms an initial dataset, from which data is then pulled to carry out the third stage 300 of the data collection and classifier training procedure. With reference to FIG. 4, first at step 301 of this third stage 300, the subject datasets in the datastore are divided into two seventy groups; non-OSA group with AHI<15, and OSA group with AHI≥15. Next, the entire initial dataset is divided into training and blind testing datasets, as shown at 302A, 302B. Within the training dataset, subject datasets with AHI and AHI≥20 are identified at 303A, 303B for feature extraction, with those of AHI≤10 denoting a low severity group and those of AHI≥20 denoting a high seventy group. It will be appreciated that the particular AHI threshold values selected to distinguish between high-severity and low-severity groups of test subjects may be varied from these specific examples of AHI≤10 and AHI≥20. Records in the training dataset with 10<AHI<20, identified at 303C, are not used for feature extraction, but are recombined with the other members of the training dataset at step 307 for inclusion included in the subsequent classifier training process described further below.

Within each of the training and blind datasets the subject datasets are subdivided into anthropometrically distinct subsets ("anthropometric subsets", for short) based on the anthropometric information, as shown at 304A, 304B, 304C. Each anthropometric subset has the subject datasets of the subjects within a certain anthropometric category (ex. BMI<35, Age ≤50 and >50, Male, female, NC>40, MpS≤2, etc.). These anthropometric subsets preferably have at least 20 individuals in each of the high severity and low severity groups. Within each anthropometric subset, and using the subject datasets of the high severity and low severity groups with AHI≥20 and AHI≤0, different features are extracted at step 305 from the different signal representations (spectral, bispectral, fractal dimension & time domain). Preferred examples of the extracted features are mean, standard deviation, entropy, skewness and kurtosis, centroid, katz fractal dimension, etc. For each anthropometric subset, features are extracted from the time and frequency domains analyses of the mouth and nose breathing sound signals. The minimum bandwidth to select a feature may be set at 100 Hz.

At step 306, feature reduction for each anthropometric subgroup is performed, for example based on feature significance, feature robustness and feature correlation and redundancy. Concerning feature significance, the p-value for each feature between the two OSA severity groups of the training dataset (AHI≥20 & AHI≤10) within an anthropometric subset is computed using the unpaired t-test. Any feature with a p-value >0.05 is excluded. Concerning feature robustness, each feature is assigned a robustness score. At first, all features have robustness scores of zero. Using the individuals of the two severity groups of the training dataset (AHI≥20 & AHI≤10), small groups of 15 per OSA severity group are created. These small groups are randomly generated and shuffled until all the individuals are selected at least once. All possible combinations of the small groups generated for each severity group of the training dataset (AHI≥20 & AHI≤10) are created. For each feature and using each combination, the p-value and normality check for each small group of the two severity groups of the training dataset (AHI≥20 & AHI≤10) are computed, separately; the Lilliefors test is used for normality check (Lilliefors, 1967). If the p-value is ≤0.05 and the normality check for each severity group of the training dataset (AHI≥20 & AHI≤10) is valid, the robustness score of this feature is increased by 1 point. This process is repeated multiple times. In the end, each feature has an overall robustness score. The features with an overall robustness score >0.6 of the maximum robustness score are selected for further analysis. Concerning feature correlation and redundancy, the available subject datasets of the two severity groups of the training dataset (AHI≥20 & AHI≤10) are used together with a support vector machine classifier to compute the training accuracy, specificity, and sensitivity for each feature in each anthropometric subset of the training dataset. All correlation coefficients between any two features are computed. Any set of features with in-between correlation coefficient ≥0.9 are removed except the feature with the highest training classification accuracy, specificity, and sensitivity. By the end of this stage, the final set of features for each subset is selected.

At step 307, the selected features for each anthropometric subset are evaluated using the total training data and the blind testing dataset separately. Next at step 308, using the training data for each OSA severity group of each anthropometric subset separately, the outliers for each feature (outside the upper and lower adjacent values of boxplot) are removed, and the upper and lower adjacent values of boxplot are recorded (Benjamini, 1988; Tukey, 1977). At step 309, using the recorded boundaries, any outside values are removed from the blind testing features.

Figure 5:
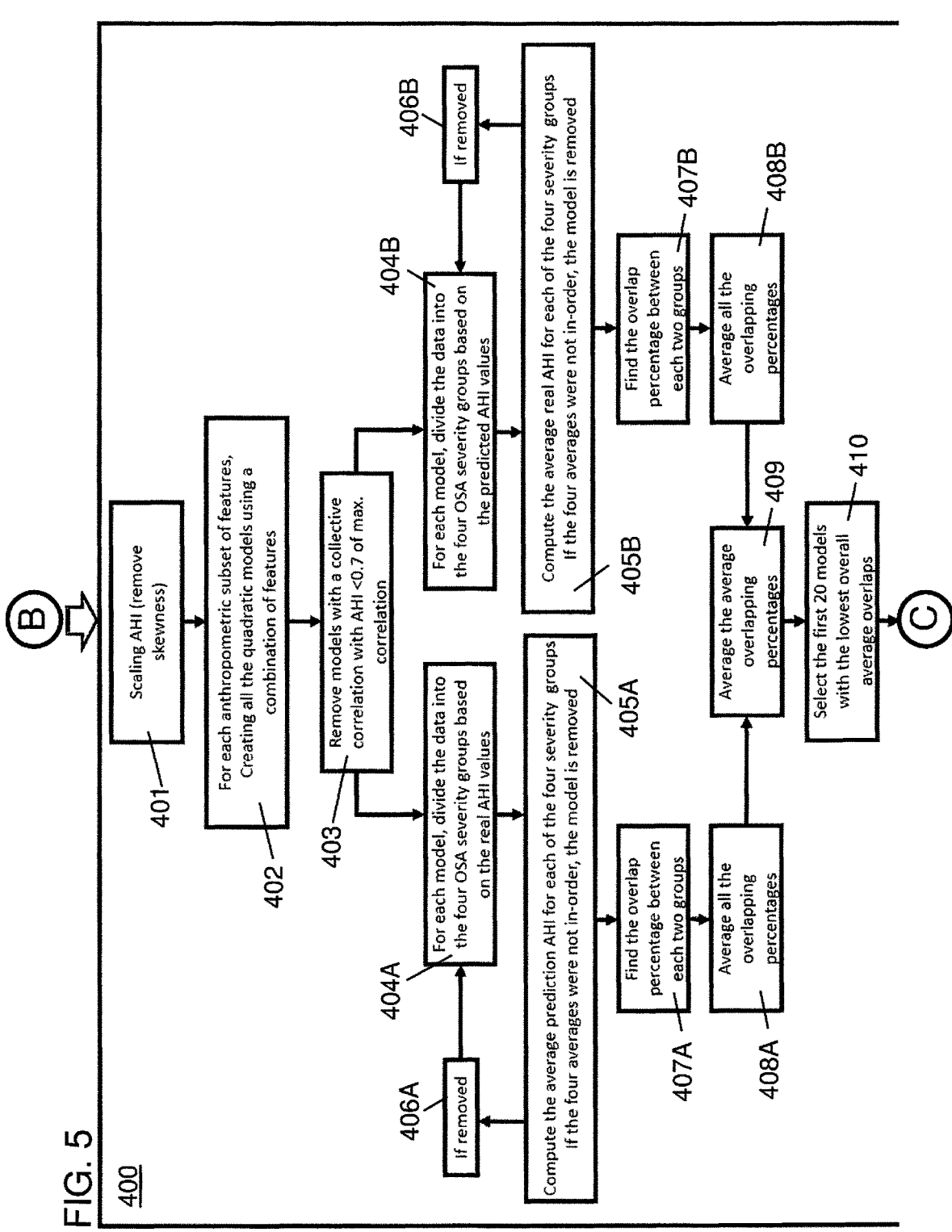
FIG. 5 is a flowchart sequence illustrating an initial portion of a fourth model-creation and model selection stage of the subject data collection and classifier training process.

Turning to FIG. 5, which shows a fourth stage 400 of the data collection and classifier training procedure, the response/dependant-variable/output should be a numerical or ordinal variable that has an increasing severity nature with either an increasing/decreasing change in its value; and so AHI is used as the response. The response should be close to a Gaussian distribution, or should be scaled to achieve a Gaussian distribution, as shown at step 401. First, the skewness of the response is checked, and if its absolute value is more than one, the response is scaled; if the skewness is positive, its logarithm is taken, and if it is negative, its square value is taken.

Next, at step 402, a linear model for the AHI using the anthropometric and sound features is built so that it holds the interaction effect between the used features. Therefore, a second-order interaction polynomial model of n variables (i.e., a combination of the features) is generated for the AHI parameter; see Eq.1 for the polynomial model (X is the used feature). The models are created for all possible feature-combinations. Each model produces a new array of values representing AHI.

$$\text{Predicted } PSG \text{ Parameter} = a_0 + \sum_{i=1}^{n} a_i X_i + \sum_{i=1}^{n} \sum_{j=i+1}^{n} a_{i,j} X_i * X_j \quad (1)$$

With reference to a first step of model reduction at step 403, the overall correlation between the prediction model and the AHI might be deceiving, as the overall linearity might neglect some regional non-linearity; so it is desirable to find the most linear model with less variance. Therefore, at step 403, the range of the response variable is divided into segments. These segments are divided based on OSA severity categories, for example non-OSA (AHI<5), mild-OSA (5<AHI<15), moderate-OSA (15<AHI<30), and severe-OSA (AHI>30)); in which case there are four segments s1, s2, s3, and s4, respectively. The correlation coefficient is evaluated for each segment. Then, the four correlation values are averaged. Only the models with a correlation coefficient exceeding a certain threshold, e.g. 70% of the maximum absolute average correlation (i.e. the maximum one of the absolute values of the average correlations respectively calculated for the different models) are used for further analysis, i.e. retained in a pool of selectable models that remain available for further selection and use in subsequent steps of the process.

Next, at steps 404 to 409 an evaluation of segment overlap is made for the purpose of model reduction and selection. Steps 404A through 408A denote a first branch of this evaluation made from an AHI perspective, i.e. using the real AHI value from the subject dataset of each subject, whereas steps 404B through 408B denote a second branch of the evaluation made from a model perspective, i.e. using the predicted AHI value calculated for each subject by the model. Within each branch, an overlap percentage is evaluated between every two segments; which in the four-segment example means there are a total of six evaluations (i.e., s1-s2, s1-s3, s1-s4, s2-s3, s2-s4, and s3-s4). Note that s4 should have the most severe subjects, and s1 should have the mildest subjects. The overlap between the segments can be seen both from the AHI point of view (left branch of FIG. 5) and the model point of view (right branch). Therefore, the evaluation is done from both of the two perspectives in the preferred embodiment.

Referring first to the left branch of FIG. 5, at step 404A, for each model, the AHI-predictions calculated thereby are sorted based on their corresponding values of the actual AHI values from the subject datasets, then are divided into the four segments. Next, at step 405A, the average and standard deviation (std) of the model values are computed for each segment separately. By then, the boundaries of each segment are their mean±std. At step 406A, all the models that do not have mean values that follow $m_{4,p} > m_{3,p} > m_{2,p} > m_{1,p}$ (where $m_{x,p}$ is the mean value for segment x from the perspective p) are rejected, i.e. removed from the pool. Using the evaluated boundaries, the overlapping area for the low severity segment is above $\text{mean}_H - \text{std}_H$, however, the overlapping area for the high severity segment is below $\text{mean}_L + \text{std}_L$; the subscripts H and L denotes to the high and low severity segments, respectively. For models remaining in the pool, if the overlap exists, then the percentage of the subjects in the overlapped area with respect to all subjects is computed at step 407A. At step 408A, the average overlap percentage of the six evaluations (overlaps) are computed.

Referring now to the right branch of FIG. 5, at step 404B, for each model, the actual AHI values from the subject datasets are sorted based on their corresponding values of the prediction values calculated by the model, then are divided into the four segments; the number of subjects per segment is equal to the number of subjects selected in step 404A for each corresponding segment. Next, at step 405B, the average and standard deviation (std) of the response values are computed for each segment separately. By then, the boundaries of each segment are their mean±std. Steps 406B, 407B and 408B are performed in the same manner described for steps 406A, 407A and 408A of the left branch. At step 409, the average of the two average overlap percentages from the two perspectives of each model is computed. At step 410, the remaining models in the pool are filtered down to a subset of whose average overlap is lesser than other models, for example narrowing the pool down to the first 20 models with the lowest overlap percentage, which are selected and retained in the pool for further analyses.

Turning to FIG. 6, the fourth stage 400 continues at step 411, where the models selected at step 410 for each anthropometric subset are evaluated using the training data, then they are used to estimate the values representing the blind testing dataset. At step 412, within each anthropometric subgroup, each selected model is validated using the training data then tested using the blind testing data. For example, using AHI=15 as a threshold, a classification process is performed using a Random-Forest (RF) classifier (Breiman, 2001) with 1200 iterations, and each iteration using ⅔ of the training dataset for training and the other ⅓ for validation. The input for the classifier is the predicted AHI values of the selected model; thus denoting a one-feature RF classifier. So, for each iteration, the training dataset is divided randomly into a training group composed of ⅔ of the training dataset, and a testing group composed of the remaining ⅓ of the training dataset, and the following three evaluations are carried out:

1) Training Results
    a) Training: from the selected model, input the predicted AHI values for ⅔ of the training data; and
    (b) Evaluation: from the selected model, input the predicted AHI values for the same ⅔ of the training data, and compare the output (OSA vs. NON-OSA classification) against the actual AHI values from the same ⅔ of the training data.

2) Validation Results
    a) Training: from the selected model, input the predicted AHI values for ⅔ of the training data;
    b) Evaluation: from the selected model, input the predicted AHI values for the other ⅓ of the training data, and compare the output (OSA vs. NON-OSA classification) against the actual AHI values from the same ⅓ of the training data.

3) Testing Results
    a) Training: from the selected model, input the predicted AHI values for ⅔ of the training data;
    (b) Evaluation: from the selected model, input the predicted AHI values for the blind testing dataset, and compare the output (OSA vs. NON-OSA classification) against the actual AHI values from the blind testing dataset.

A cost-matrix may be used to compensate for the difference in the sample size between the two OSA seventy sub-groups of the initial dataset (AHI≥5 & AHI<15). This procedure is repeated multiple times. Then, the validation and blind testing accuracy results are averaged for each model for use as evaluated performance metrics thereof.

At step 413, the pool of models is once again filtered or reduced by removing those of lesser evaluated performance, leaving behind a reduced quantity (e.g. five) models having the highest average validation and blind testing accuracies, at which point the balanced validation sensitivities and specificities of these models are selected and recorded. The average validation and testing classification decisions for each subject for each of these remaining models in the pool are also recorded. At the conclusion of the fourth stage 400, respective model pools for the different anthropometric subsets have accordingly been compiled, evaluated, and reduced down a group of best selected according to their evaluated performance.

Still referring to FIG. 6, the fifth stage 500 starts at step 501 starts with running different model combinations from among the best selected models that remain in the different model pools of the different anthropometric subsets; of which each model combination contains the results of a respective model from each anthropometric subgroup. Next, at step 502, a weighted classification decision per subject is calculated for each model; if the participant is classified as severe (I.E. having OSA), the validation sensitivity of the model is used as the weight, and if the participant is classified as normal (non-OSA), the -ve validation specificity of the model is used as the weight. Then, the average classification decision among the different models of each model combination is calculated for each participant subject. Then, at step 503, the overall classification, sensitivity, and specificity are calculated for the validation and testing results separately, and the best model combination providing the highest validation and blind testing accuracies with reasonable sensitivities and specificities is selected. The models of this selected best model combination are stored in computer-readable memory together with the trained classifier module to form at least a substantive portion of a computer executable OSA screening tool operable to classify screening patients as either OSA or non-OSA.

Figure 7:
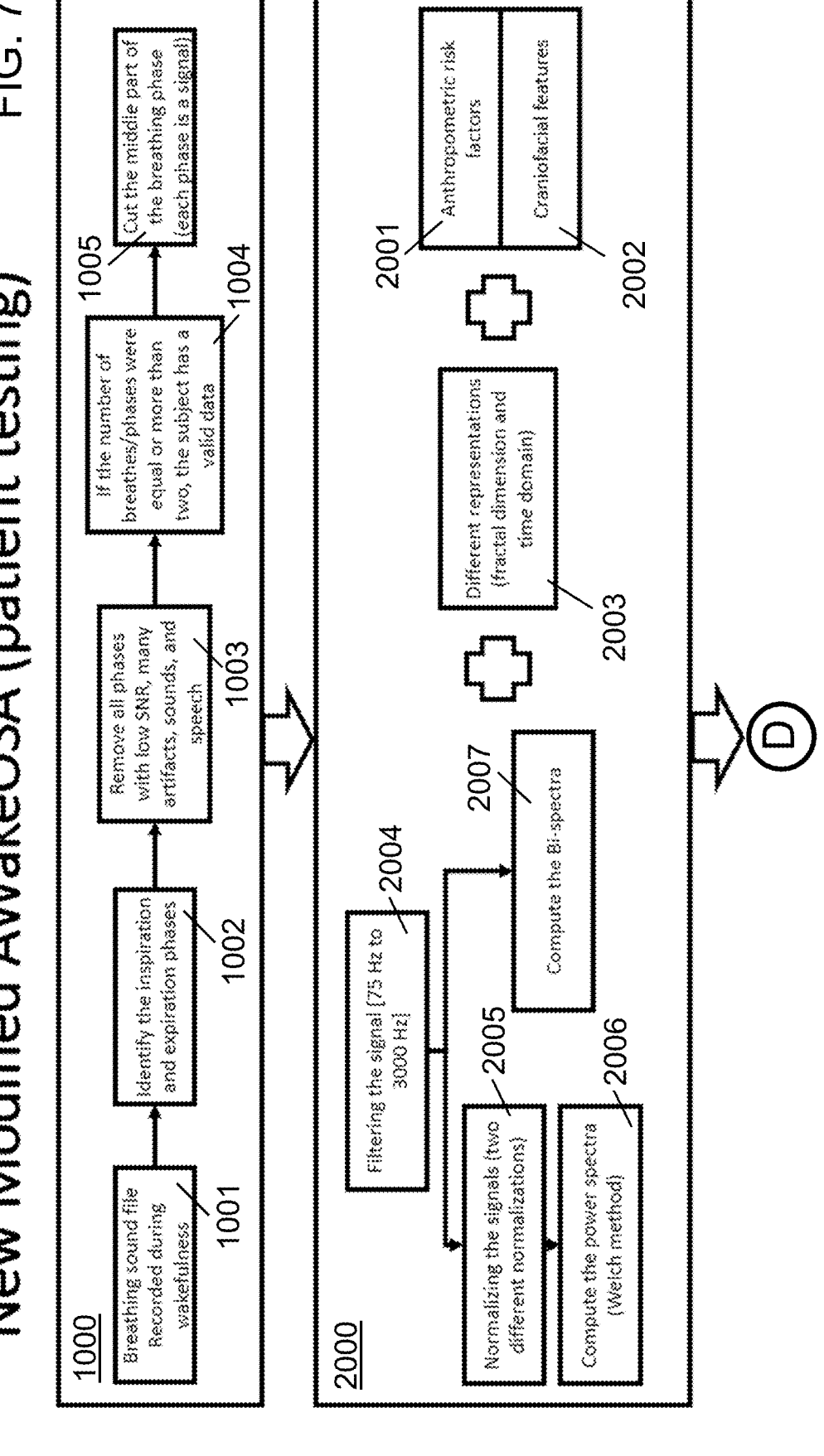
FIG. 7 is a flowchart sequence illustrating first and second data collection stages of a patient screening process for screening patients using the computerized screening tool built from the data collection and classifier training process of FIGS. 3 through 6.
Figure 8:
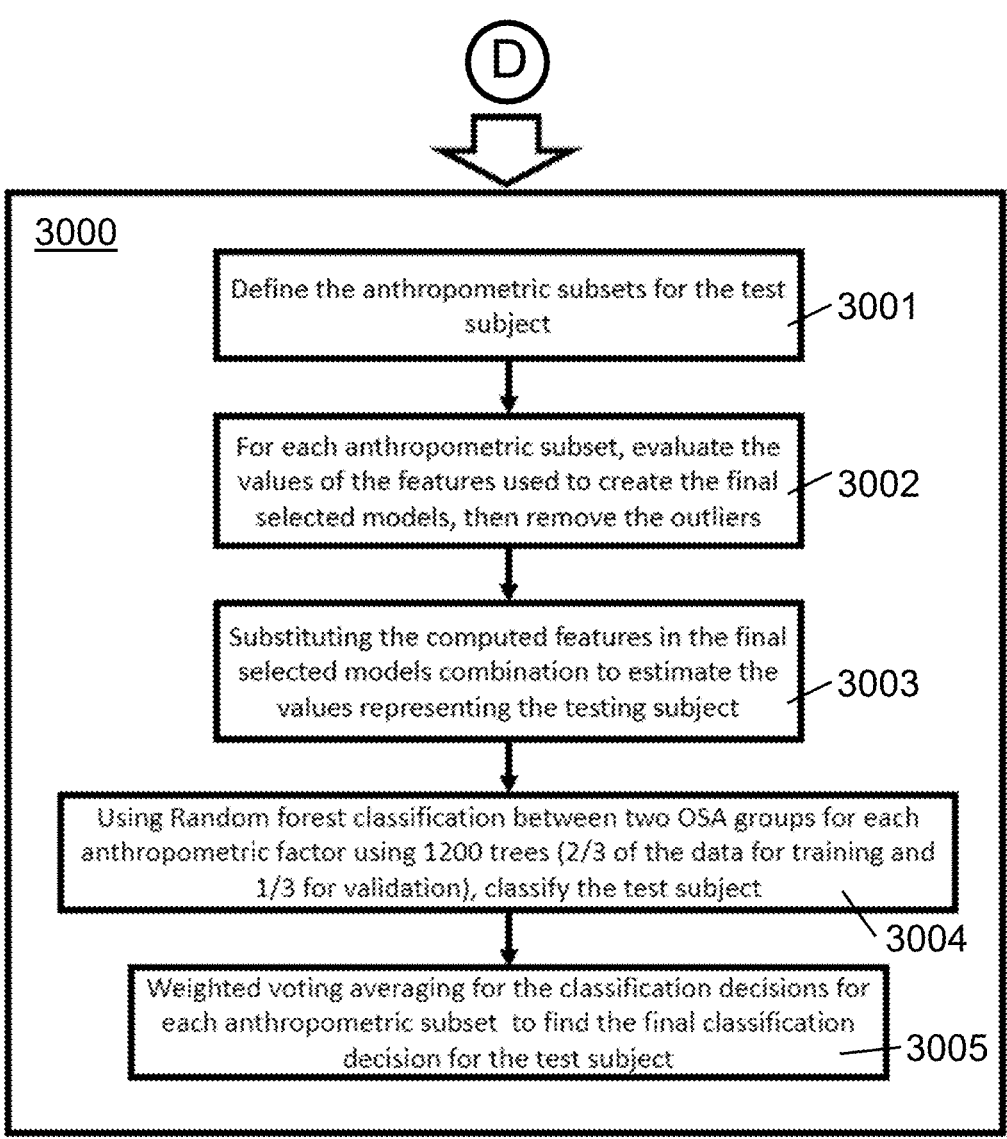
FIG. 8 is a flowchart sequence illustrating a third data processing and patient classification stage of the patient screening process.

FIGS. 7 and 8 illustrate a patient screening process for screening patients using the computerized screening tool whose trained classifier module and best model combination was derived from execution of the subject data collection and classifier training process of FIGS. 3 through 6. Referring to FIG. 7, the first and second stages 1000, 2000 shown therein are substantially the same as the first and second stages 100, 200 shown in FIG. 3 for the earlier subject data collection and classifier training process. The notable difference in FIG. 7 is that stages 1000, 2000 are being performed on a patient whose AHI is not known, as opposed to a test subject of known AHI. Accordingly, the actual AHI (208, FIG. 2) of the patient is not known, and thus not stored in a datastore on computer readable memory, in the patient screening context of FIG. 7. Otherwise, steps 1001-1005 and 2004-2007, and stored data 2001-2003, of FIG. 7 are the same as steps 101-105 and 204-207, and stored data 201-203, of FIG. 3, but stored for a "patient" rather than a "subject", and is thus now referred to as a patient dataset.

Turning to FIG. 8, in the third stage 3000 of the patient screening process, the anthropometric information from the patient dataset is first compared against the same anthropometric categories that were previously used to subdivide the training and blind testing datasets into anthropometric subsets back at step 304 of in FIG. 3, whereby each patient is assigned to a subset of anthropometric categories at step 3001. At step 3002, the best audio signal features for classifying the patient, identified as those that are relied on by the respective best models that are stored in the best model combination for the particular anthropometric categories to which the patient has been matched (patient-matched models), are then extracted and evaluated from the stored signal representations (spectral 2006, bispectral 2007, fractal dimension & time domain 2003) in the patient dataset. At this step, any outliers are removed according the previously recorded boundaries from step 308. At step 3003, the extracted and evaluated features from the patient dataset are run through the patient-matched models from the stored best model combination, thereby calculating estimated AHI values for the patient. Then, at step 3004, a classification decision (OSA vs. non-OSA) using the trained random forest classifier is evaluated for each patient-matched anthropometric model using the predicted AHI value therefrom, which is then followed at step 3005 by calculation of a weighted voting average of the classification results from the different patient-matched anthropometric models. The resulting weighted voting average denotes the final classification decision for the screening patient, which is recorded in the patient dataset in the datastore, and preferably is shown on a visual display of the computer 18 running the screening tool, or another computer or device connected thereto over a network.

While the basic system architecture shown in FIG. 1 is described as usable to execute both the subject data collection and classifier training procedure of FIGS. 3 through 6, and the patient screening procedure of FIGS. 7 and 8, it will be appreciated that the computerized screening tool derived from the process of FIGS. 1 through 6 may be stored and executed on a separate computer. Also, while a single computer is shown, it will be appreciated that modules or other subcomponents of the executable software stored in computer readable memory for execution by one or more computer processors to execute the various processes described herein, it will be appreciated that such software may be distributed across any number of computer readable media for execution by any number of computer processors embodied in any number of computers interconnected by an appropriate local area or wide area network.

Experimental Support

Experiment A

The use of tracheal breathing sounds analysis for screening OSA was investigated. Breathing sounds recorded from the mouth and nose were first sequestered into inspiratory and expiratory sounds; then, the characteristic features were extracted by spectral, bispectral and fractal analyses, followed by a classification routine for estimating the severity of OSA.

It is hypothesized that the upper airway (UA) deformities due to OSA affects the breathing sounds even during wakefulness, and that effect should be detectable by tracheal breathing sounds analysis (Finkelstein et al., 2014; Lan et al., 2006; Moussavi, Z. et al., 2015). In prior works (Elwali & Moussavi, 2017; Karimi, 2012; Montazeri et al., 2012; Moussavi, Z. et al., 2015), proof of concept was shown for this hypothesis. Subsequently a testing classification accuracy of ~84% with comparable (<10% difference) specificity and sensitivity for two balanced groups of non-OSA (AHI≤5, n=61) and OSA (AHI≥10, n=69) (Elwali & Moussavi, 2017) was achieved. A significant superiority of using tracheal breathing sound features over the use of only anthropometric information (i.e., sex, age, neck circumference) for screening OSA during wakefulness was also shown (Elwali & Moussavi, 2017). However, the effects of the anthropometric confounding variables (i.e., age, sex, height, etc.) on the sound signals were not investigated in such prior work. In addition, as it is desirable to achieve quick screening with high sensitivity of identifying the OSA individuals in need of treatment, it is desirable to have only one threshold (e.g., AHI=15) for such decision making. Although it is difficult to distinguish an AHI of 14 and 16 from each other, the AHI=15 was chosen as the threshold because it is the most common clinically accepted threshold to separate OSA individuals in need of treatment from those who do not benefit from a treatment (Lifter, 2007; Medscape, Aug. 23, 2016). When prior techniques were applied with this threshold AHI=15, the blind-test accuracy dropped to <70%, which is not desirable. It is commonly discussed that AHI is not the best indicator of a diagnostic decision for OSA. Sleep medicine doctors usually base their decision on several factors such as daytime sleepiness, number of arousals/night, etc. along with AHI. However, for a quick screening with automated real-time screening, reference is needed for accuracy, and AHI is the most common standard used. Therefore, the presently disclosed solution uses anthropometric information and a few minutes of tracheal breathing sounds recorded during wakefulness to identify OSA individuals in need of treatment. The AWakeOSA algorithm considers the confounding anthropometric effects on the breathing sounds and uses them to predict the severity of OSA in a subgroup with a similar confounding variable.

Figure 14:
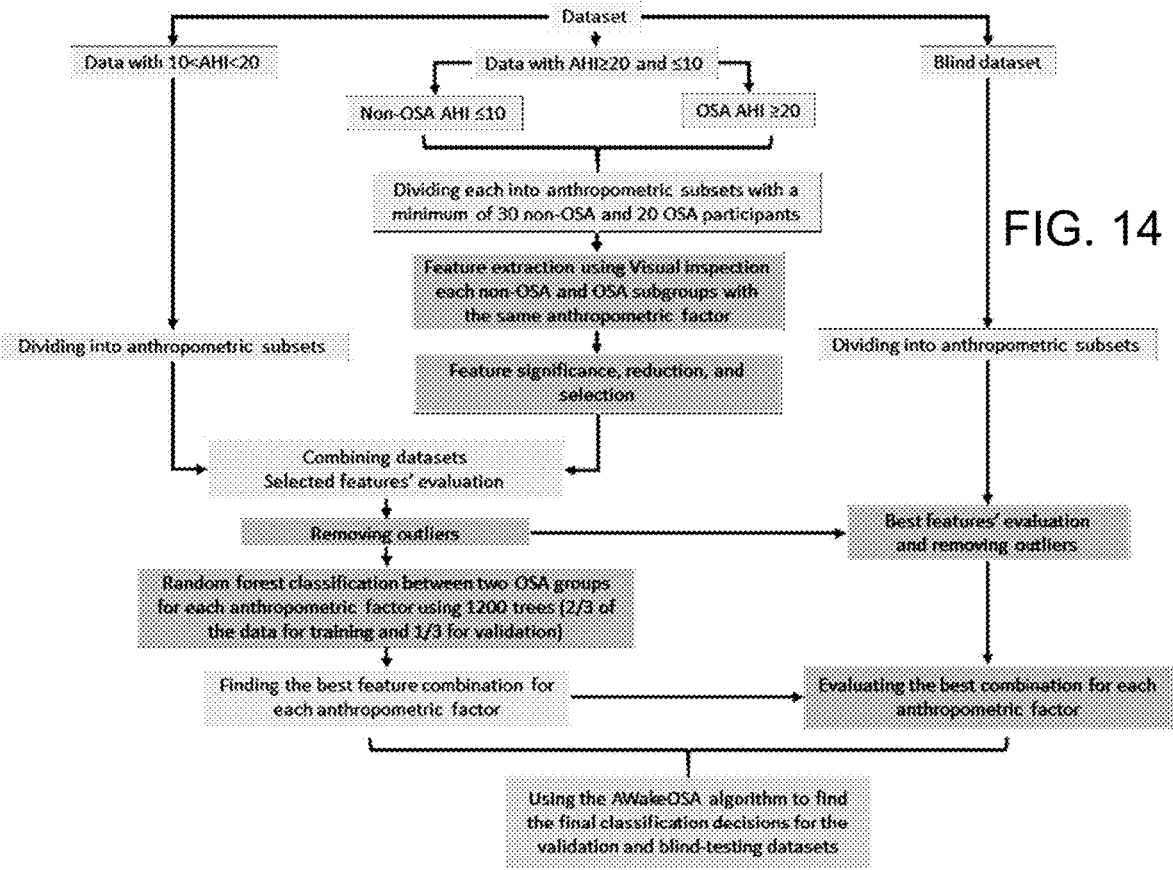
FIG. 14 is a flowchart sequence illustrating steps of the simplified subject data collection and classifier training process of FIG. 10.

The premise of the AWakeOSA algorithm is to find the best sound features sensitive to OSA severity (determined by AHI) for each subgroup of individuals with a specific anthropometric factor (i.e., age, sex, weight, etc.). A simplified variant of the algorithm tested in Experiment A is represented schematically in FIG. 10, and shown in more detail in the flowchart sequence of FIG. 14, which includes the same feature reduction and selection stage 300 of FIG. 4, but omits the subsequent model-building, model-selection and model combining stages of FIGS. 5 and 6 of the more detailed embodiment shown in therein. Since the OSA population is very heterogeneous and many confounding variables such as age, sex, height, weight, etc. affect breathing sound characteristics (Barsties, Verfaillie, Roy, & Maryn, 2013; Linville, 2001; Titze, 2000; Torre III & Barlow, 2009), it is challenging to have some sound features predicting AHI for all individuals. The simplified AWakeOSA algorithm overcomes this challenge by grouping individuals into subgroups based on their specific anthropometric factors that in turn affect breathing sounds. Then, in each subgroup, the best sound features to predict AHI are extracted, and a classifier is trained using a training set of data. The classifiers' outcomes in each subgroup are then used in a weighted average voting scheme to make the classification decision OSA (AHI>15) or non-OSA (AHI<15).

The follow summarizes the procedure and results of a first experimental use of the simplified AWakeOSA algorithm for an AHI=15 as the threshold for data collected from 199 individuals with various severity of OSA (AHI was between 0 to 143, out of which about 45% of data were set aside as a blind test and the remaining was used for extracting features and training the classifiers. In all instances, a two-group classification algorithm based on the Random-Forest algorithm (Breiman, 2001) was used, though it will be appreciated that in other working embodiments of the present invention, a different type of classification algorithm may alternatively be employed.

The breathing sounds data of 199 participants made up of 109 non-OSA individuals (50 males, AHI<15) and 90 OSA individuals (66 males, AHI>15) were used. All data were recorded during wakefulness in the evening (~8 PM) before the participants proceed to PSG sleep study. While the detailed working examples use AHI and breathing sounds specifically, other embodiments may make use of an OSA severity parameter other than AHI, and/or alternative audible recordings, such as speech. Anthropometric parameters for the two groups are reported in Table 1. The data of the two severity groups of the initial dataset (AHI≥15 & AHI<15) were not matched in terms of any of the confounding variables: sex (male/female), body mass index (BMI threshold=35), neck circumference (NC threshold=40), age (threshold=50), or Mallampati score (MpS threshold=3). Out of the 199 individuals' dataset, 86 individuals' (47 non-OSA and 39 OSA) data were set aside as a blind test for assessing the algorithm's accuracy. Table 1 also shows the anthropometric information for the two severity groups (AHI≥15 & AHI<15) of the training and testing datasets.

TABLE 1

| PARTICIPANTS' ANTHROPOMETRIC INFORMATION. | | | | | | | | |
|---|---|---|---|---|---|---|---|---|
| | | Age | | | BMI | | NC | |
| | $AHI_{Supine}$ | n > 50 | n ≤ 50 | Sex | n ≥ 35 | n < 35 | n > 40 | n ≤ 40 | MpS |
| The entire dataset (199 subjects) | | | | | | | | | |
| Non-OSA (AHI < 15, n = 109) | 3.6 ± 4.0 | 48.6 ± 12.7 50 | 59 | 50 M, 59 F | 31.8 ± 7.2 28 | 81 | 39.8 ± 5.1 50 | 59 | 59 'I', 25 'II', 15 'III' and 9 'IV' |
| OSA (AHI ≥ 15, n = 90) | 42.9 ± 32.7 | 52.2 ± 11.6 52 | 38 | 66 M, 24 F | 36.4 ± 8.0 44 | 46 | 44.1 ± 3.7 72 | 18 | 22 'I', 30 'II', 22 'III' and 16 'IV' |
| The training dataset (113 subjects) | | | | | | | | | |
| Non-OSA (AHI < 15, n = 62) | 3.4 ± 3.7 | 49.2 ± 12.9 30 | 32 | 32 M, 30 F | 31.7 ± 7.4 18 | 44 | 40.1 ± 5.2 32 | 30 | 32 'I', 14 'II', 11 'III' and 4 'IV' |
| OSA (AHI ≥ 15, n = 51) | 52.8 ± 39.9 | 52.0 ± 12.0 29 | 22 | 36 M, 15 F | 37.3 ± 9.0 25 | 26 | 43.9 ± 3.9 39 | 9 | 13 'I', 14 'II', 16 'III' and 8 'IV' |

TABLE 1-continued

PARTICIPANTS' ANTHROPOMETRIC INFORMATION.

| | | Age | | | BMI | | NC | | |
|---|---|---|---|---|---|---|---|---|---|
| $AHI_{Supine}$ | n > 50 | n ≤ 50 | Sex | n ≥ 35 | n < 35 | n > 40 | n ≤ 40 | MpS |
| | | | | The Blind testing dataset (86 subjects) | | | | | |
| Non-OSA (AHI < 15, n = 47) | 3.9 ± 4.3 | 47.8 ± 12.5 20 | 27 | 18 M, 29 F | 31.9 ± 7.0 10 | 37 | 39.5 ± 5.1 18 | 26 | 27 'I', 11 'II', 4 'III' and 5 'IV' |
| OSA (AHI ≥ 15, n = 39) | 29.9 ± 17.6 | 52.5 ± 11.0 23 | 16 | 30 M, 9 F | 35.3 ± 6.4 19 | 20 | 44.3 ± 3.5 33 | 6 | 9 'I', 16 'II', 6 'III' and 8 'IV' |

LEGEND: AHI: APNEA-HYPOPNEA INDEX, BMI: BODY MASS INDEX, NC: NECK CIRCUMFERENCE, MPS: MALLAMPATI SCORE, M/F: MALE/FEMALE.

AHI was found to have significant correlations with BMI, NC, and MpS (r=0.44, 0.43, and 0.26, respectively). However, when the available anthropometric information (i.e., BMI, age, NC, and sex) of the STOP-BANG questionnaire (Nagappa et al., 2015) was used, and the entire dataset (199 subjects) for the two OSA severity groups (with AHI=15 as a threshold) was classified, the resulted classification accuracy, specificity, and sensitivity were found to be only 63.4%, 74.3%, and 50.5%, respectively.

The recorded breathing sounds collected from four breathing maneuvers (i.e., Mouth and Nose—inspiration and—expiration) were analyzed. While a sharp threshold of AHI=15 was used for training classifiers, for the feature extraction and reduction stage, only data of subjects with AHI≤10 (n=60) and AHI≥20 (n=40) in the training dataset were used. Using the algorithm schematically shown in FIG. 10, the recorded breathing sounds were analyzed in each of the following anthropometric subsets of the training dataset separately: BMI<35, Age >50, Age ≤50, male, NC>40, and MpS≤2. Subjects in each anthropometric subset were matched with respect to only one anthropometric variable. There were no subsets of BME>35 or NC<40, etc. due to limited sample size. The selected and used subsets had ≥30 non-OSA subjects and ≥20 OSA subjects, which were reasonable numbers for feature extraction and reduction and group classification.

The number of breathing sound features extracted from the two breathing maneuvers, while analyzing inspiratory and expiratory phases separately, was around 250. Using the novel feature reduction procedure (FIGS. 4 & 14) on the training dataset, around 15 features per each anthropometric subset were selected for further investigation. These sound features showed significant differences (p<0.05) between the two OSA severity groups (AHI≥15 & AHI<15) as they were highly correlated (p<0.01) with AHI. In addition, they showed an effect size >0.8. Table 2 shows the selected sound features' definition, breathing maneuver, investigated subset, and their correlation coefficient with AHI.

TABLE 2

DESCRIPTIONS AND DETAILS OF THE SELECTED FEATURES.

| FN | BM | Feature's definition | Subset | CC |
|---|---|---|---|---|
| 1 | ExpM | $_{f1=130}^{f2=235}$Mean of P(f) − $_{f1=1260}^{f2=1410}$Mean of P(f) | All data | −0.40 |
| 2 | InsN | $_{f1=250}^{f2=355}$Mean of the slope of P(f) | All data | 0.37 |
| 3 | ExpM | $_{f1=300}^{f2=550}$Bandwidth of the spectral centroid of P(f) | All data | −0.48 |
| 4 | InsM | $_{f1=1200}^{f2=1515}$First order moment of the positive diagonal of B(f, f) | All data | 0.25 |
| 5 | InsM | $_{f1=140}^{f2=270}$Gmean of P(f) | BMI <35 | −0.41 |
| 6 | InsM | $_{f1=140}^{f2=270}$First order moment of B(f, f) on 0.5f − f line | BMI <35 | −0.45 |
| 7 | InsN | $_{f1=130}^{f2=275}$Mean of B(f, f) | BMI <35 | −0.40 |
| 8 | InsN | $_{f1=min}^{f2=max}$Weight center of the positive diagonal of B(f, f) | BMI <35 | 0.43 |
| 9* | InsN | $_{f1=130}^{f2=280}$Mean of P(f) | Age >50 | −0.35 |
| 10* | InsN | $_{f1=80}^{f2=560}$Spectral centroid of P(f) | Age >50 | 0.37 |
| 11 | InsM | $_{f1=130}^{f2=230}$Weight center of the positive diagonal of B(f, f) | Age >50 | 0.32 |
| 12 | InsN | $_{f1=130}^{f2=280}$Mean of B(f, f) | Age >50 | −0.37 |
| 13 | InsN | $_{f1=130}^{f2=280}$Second order moment of the negative diagonal of B(f, f) | Age >50 | −0.48 |
| 14 | InsN | $_{f1=270}^{f2=370}$Mean of the slope of P(f) | Age ≤50 | 0.52 |
| 15 | ExpN | $_{f1=450}^{f2=550}$Mean of the slope of P(f) | Age ≤50 | −0.41 |
| 16 | InsM | $_{f1=390}^{f2=510}$Weight center of B(f, f) on 0.5f − f line | Age ≤50 | 0.40 |
| 17 | InsN | $_{f1=250}^{f2=350}$Mean of the slope of P(f) | Male | 0.42 |
| 18 | InsN | Frequency of the first peak for of P(f) with a cuttoff of 550 Hz | Male | 0.53 |
| 19 | InsN | $_{f1=395}^{f2=520}$Mean of P(f) | NC >40 | 0.37 |
| 20 | InsM | $_{f1=60}^{f2=600}$Frequesncy of the average of Maximum peaks of P(f) | NC >40 | 0.29 |
| 21 | InsM | $_{f1=60}^{f2=600}$Weight center of B(f, f) on f − 2f line | NC >40 | 0.35 |
| 22 | InsN | $_{f1=395}^{f2=520}$Weight center of the positive diagonal of B(f, f) | NC >40 | 0.28 |
| 23 | InsN | $_{f1=250}^{f2=350}$Mean of the slope of P(f) | MpS <3 | 0.34 |
| 24 | InsM | $_{f1=1090}^{f2=1460}$Weight center of B(f, f) on f − 2f line | MpS <3 | 0.27 |

TABLE 2-continued

DESCRIPTIONS AND DETAILS OF THE SELECTED FEATURES.

| FN | BM | Feature's definition | Subset | CC |
|----|----|----|----|----|
| 25 | InsM | $f1-1260$ $f2-1460$ First order moment of B(f, f) on f – 2f line | MpS <3 | 0.39 |
| 26 | ExpM | $f1-1260$ $f2-1410$ First order moment of the negative diagonal of B(f, f) | MpS <3 | 0.36 |

*Features 9 and 10 were used alternatively
LEGEND: INS/EXP: INSPIRATION/EXPIRATION, M/N: MOUTH/NOSE, MEAN: ARITHMETIC MEAN, GMEAN: GEOMETRIC MEAN, P(F): THE POWER SPECTRUM, B(F, F): THE BISPECTRUM, F: FREQUENCY, FN: FEATURE NUMBER, BM: BREATHING MANEUVER, SUBSET: SUBSET OF USAGE, BMI: BODY MASS INDEX, NC: NECK CIRCUMFERENCE, MPS: MALLAMPATI SCORE, CC: THE CORRELATION COEFFICIENT WITH AHI. ALL CORRELATIONS WERE SIGNIFICANT AT p < 0.01 LEVEL.

In the next stage of the simplified AWakeOSA algorithm, the selected sound features and one anthropometric feature, the NC, were used as the features for classification because it showed a significant correlation (0.43, with p<0.01) with AHI when tested on the training dataset. The NC feature was investigated further in all subsets other than its own subset. Thus, the selected sound features and NC were divided into three- and four-feature combinations. These feature combinations were used to classify each participant's data in every subset to one of the two OSA severity classes (AHI≥15 & AHI<15). Table 2 column 4 shows the sound features used per anthropometric subset constructing the combination for classification. NC was selected and used in age 50 and male subsets.

Figure 11:
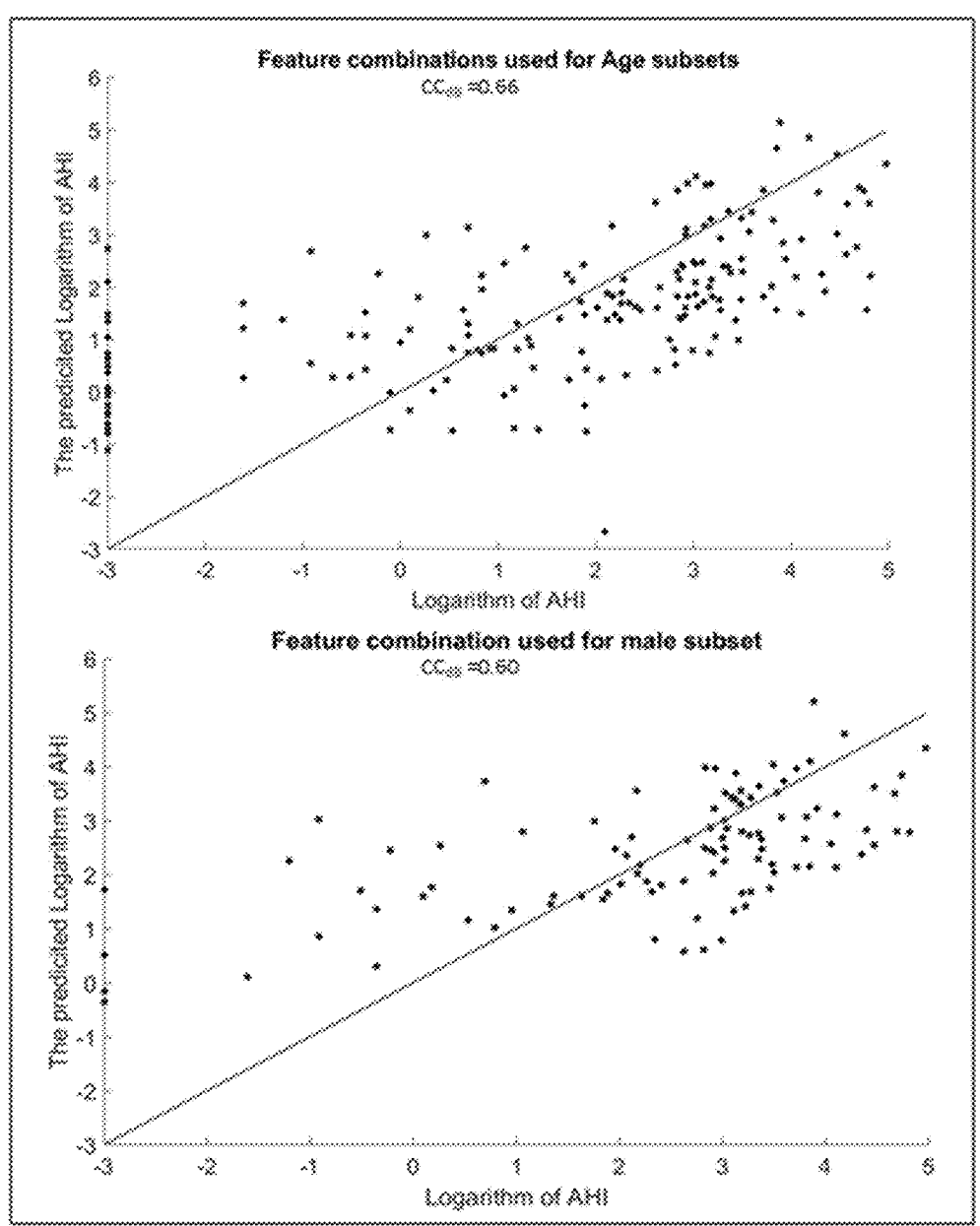
FIG. 11 illustrates, from a first experiment using the simplified variant of FIG. 10, regression models of feature combinations selected for age ≤50 (top) and male (bottom) subsets with the logarithm of AHI, in which solid dots show the estimated logarithm of AHI values by the model, AHI is: apnea-hypopnea index, and CC is correlation coefficient.

Table 3 shows the classification accuracy, specificity, and sensitivity for the out of the bag-validation using Random-Forest classification (Breiman, 2001) and for the blind testing dataset for each anthropometric subset separately as well as the final voted classification. In addition, Table 3 shows the correlation coefficient between AHI/logarithm (AHI) and each of the feature combinations using the linear regression analysis. FIG. 11 shows the linear regression analysis outcomes of the selected feature combinations selected for age ≤50 and male subsets with the AHI in logarithmic scale. Furthermore, feature combination selected for age ≤50 showed the highest testing classification accuracy of 86% within its own subgroup. When this feature combination used for the entire training dataset and blind data set, it resulted in 71.6% accuracy for out of the bag-validation of the training set and 75.6% for the blind testing data.

Figure 10:
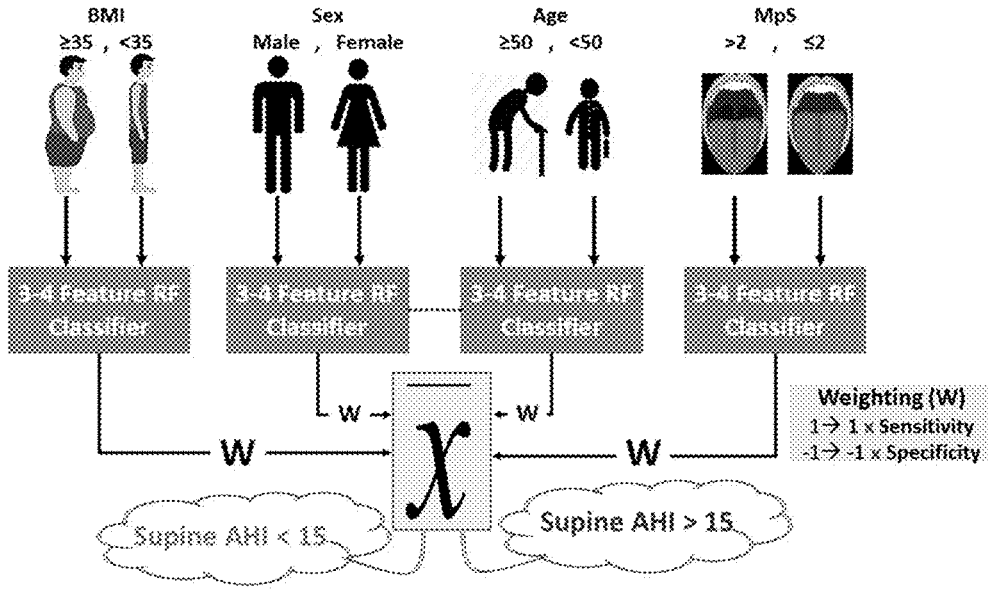
FIG. 10 schematically represents a simplified variant of the subject data collection and classifier training process of FIGS. 3 to 6.
Figure 12:
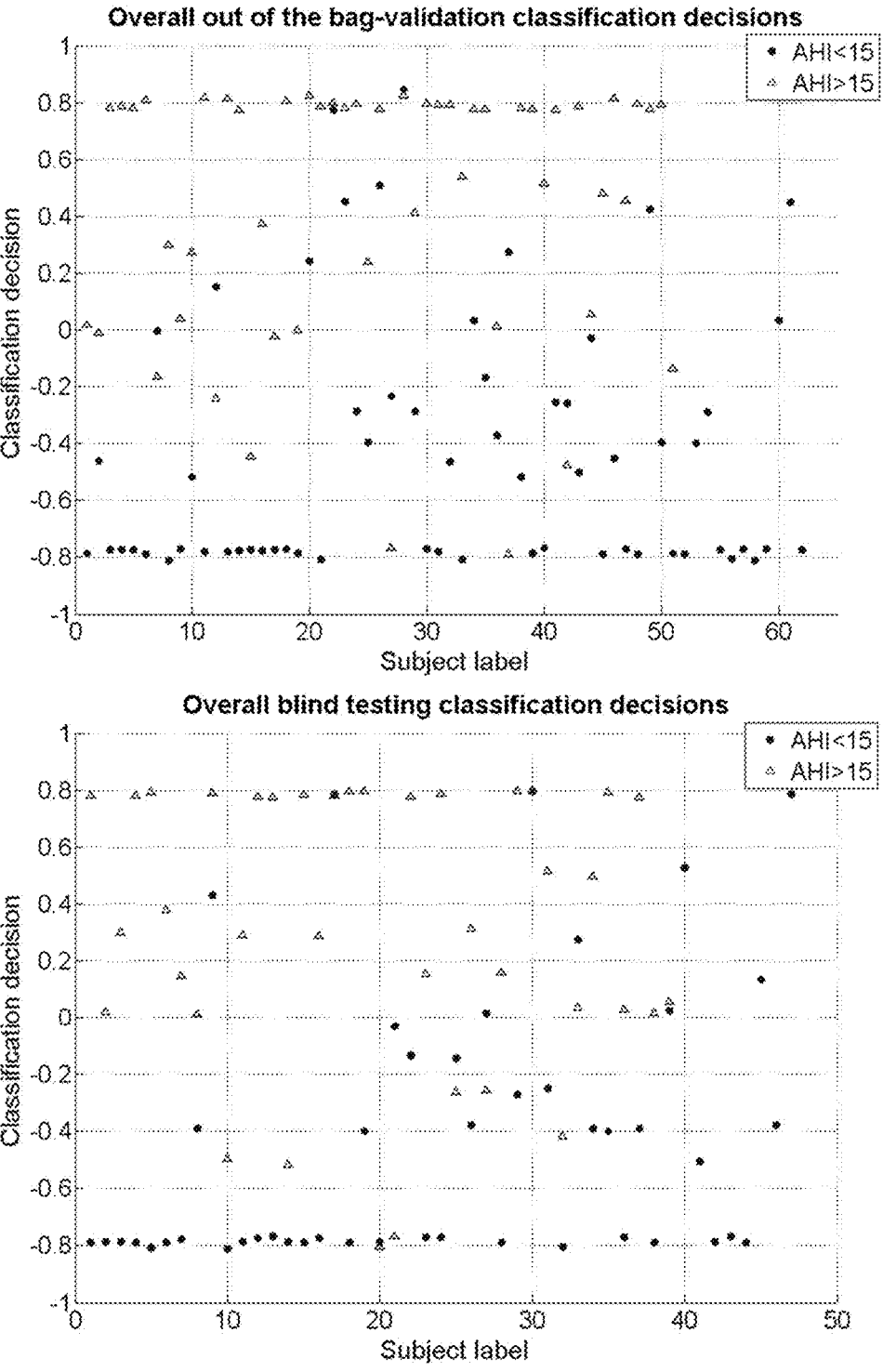
FIG. 12 shows, from the first experiment, scatter plots for out of the bag-validation in a training dataset (top) and a blind testing set's (bottom) classification decisions, in which round and triangular plot points represent non-OSA and OSA individuals, respectively.

The overall classification results using the proposed weighted linear voting scheme, illustrated in FIG. 10, were found to be 82.3%, 82.3%, and 81.4% for classification accuracy, specificity, and sensitivity for the out of the bag-validation, and 81.4%, 80.9%, and 82.1% for classification accuracy, specificity, and sensitivity for the blind testing data, respectively. FIG. 12 shows the scatter plot for overall out of bag-validation (top) and blind (bottom) testing classification decisions. A classification decision of 1 (considering 100% for both specificity and sensitivity) means that all the used Random-Forest classifiers of each anthropometric subset voted the subject into the OSA group, while classification decision of –1 (considering 100% for both specificity and sensitivity) means all the used Random-Forest classifiers of each anthropometric subset voted the subject into the non-OSA group.

Anthropometric information of the misclassified subjects in both out of bag-validation and blind testing classification are listed in Table 4. Out of 109 non-OSA subjects, 20 were misclassified to the OSA group, and out of 90 OSA subjects, 16 were misclassified to the non-OSA group. Investigation was also made of whether removing a subset's decision from the voting stage in the simplified AWakeOSA algorithm would improve or degrade the overall classification results. The results indicated removing any of the subsets decreases the classification performance by 2.5-8%.

TABLE 3

CORRELATION COEFFICIENT (CC) OF EACH FEATURE COMBINATION AND AHI AND CLASSIFICATION RESULTS USING FEATURE COMBINATIONS FOR EACH ANTHROPOMETRIC SUBSET SEPARATELY.

| Groups | $CC/CC_{dB}$ | Out of bag-validation | | | Blind testing | | |
|----|----|----|----|----|----|----|----|
| | | Accuracy | Sensitivity | Specificity | Accuracy | Sensitivity | Specificity |
| BMI < 35 | 0.46/— | 78.9% | 81.8% | 74.1% | 68.4% | 75.7% | 55.0% |
| Age > 50 | 0.52/— | 81.7% | 83.3% | 80.0% | 67.4% | 60.0% | 73.9% |
| Age ≤ 50 | 0.63/0.66 | 85.7% | 84.4% | 87.5% | 86.0% | 85.2% | 87.5% |
| Male | 0.49/0.60 | 75.0% | 71.9% | 77.8% | 64.6% | 66.7% | 63.3% |
| NC > 40 | 0.43/— | 75.0% | 75.0% | 75.0% | 64.7% | 66.7% | 63.6% |
| MpS ≤ 2 | 0.47/0.51 | 73.3% | 71.7% | 75.9% | 74.6% | 81.6% | 64.0% |
| | | Final voted results | | | | | |
| Voted Accuracies | — | 82.3% | 81.4% | 82.3% | 81.4% | 82.1% | 80.9% |

LEGEND: CCDB: CC WITH THE LOGARITHM OF AHI, BMI: BODY MASS INDEX, NC: NECK CIRCUMFERENCE, MPS: MALLAMPATI SCORE.

TABLE 4

ANTHROPOMETRIC INFORMATION OF ALL MISCLASSIFIED SUBJECTS WITHIN THE
TRAINING DATASET (OUT OF THE BAG-VALIDATION) AND BLIND TESTING DATA.

|  | AHI | Age | Sex | BMI | NC | MpS |
|---|---|---|---|---|---|---|
| Non-OSA (AHI < 15, n = 20) | 3.1 ± 3.1 | 45.9 ± 13.6 | 13 M, 7 F | 36.7 ± 7.6 | 43.2 ± 3.4 | 13 'I', 4 'II', 2 'III' and 1 'IV' |
| OSA (AHI > 15, n = 16) | 37.0 ± 28.3 | 54.2 ± 11.8 | 13 M, 3 F | 34.4 ± 6.9 | 43.3 ± 3.6 | 5 'I', 6 'II', 4 'III' and 1 'IV' |
| Total (n = 36) | 18.2 ± 25.3 | 49.6 ± 13.3 | 26 M, 10 F | 35.7 ± 7.3 | 43.2 ± 3.4 | 18 'I', 10 'II', 6 'III' and 2 'IV' |

LEGEND: NC: NECK CIRCUMFERENCE, BMI: BODY MASS INDEX, MPS: MALLAMPATI SCORE.

Undiagnosed severe OSA significantly increases the healthcare cost and the risk of perioperative morbidity and mortality (American Society of Anesthesiologists, 2006; Gross et al., 2014). Anthropometric measures have been shown to have a high sensitivity in screening OSA (El-Sayed, 2012; Nagappa et al., 2015) but at the cost of a very poor specificity (~36%) (Nagappa et al., 2015). This might be in part due to the subjectivism of most of the STOP-BANG parameters. Although those parameters do not have a good classification power to screen OSA, they are correlated with AHI and also affect breathing sounds (Barsties et al., 2013; Linville, 2001; Nagappa et al., 2015; Titze, 2000; Torre III & Barlow, 2009). In the dataset of Experiment A, anthropometric parameters had a correlation of 0.03<|r|≤0.44 with AHI, and 0.00<|r|≤0.5 with breathing sounds. Previously, it was shown that breathing sounds have a much higher classification power for screening OSA than the anthropometric features (Elwali & Moussavi, 2017). When only sound features were used for classification of OSA severity with a sharp AHI=15, the classification accuracies were found to be 79.3% and 74.4% for out of bag-validation and blind testing, respectively. These accuracies are much higher than what STOP-BANG questionnaire can provide (63.4%) but not high enough nor sufficient for a reliable (robust) OSA screening during wakefulness.

In order to increase the accuracy and reliability of using breathing sounds to screen OSA during wakefulness, the simplified variant shown schematically in FIG. 10 uses the anthropometric features to subgroup the data and get a classification vote in each subgroup, while the final classification is based on the average vote of all subsets. This subdivision was done to reduce the impact of the confounding variables on the feature extraction stage and the classification process. The results showed that the simplified AWakeOSA voting algorithm provides a higher and more reliable blind test accuracy, even with a sharp threshold of AHI=15. The main challenge in all studies using breathing sounds analysis for wakefulness OSA screening is the heterogeneity of the population. As the cause of OSA can vary among individuals, people with the same OSA severity can have very different anthropometric features, and those differences affect respiratory sounds differently. The simplified algorithm of FIG. 10 takes into account such heterogeneity and tries to find the best sound features specific to each subset of data that share one particular important confounding variable such as age, BMI, sex, etc. On the other hand, as the effect of these features on the sounds varies, the FIG. 10 variant allows a weighting factor for each subset classifier's vote. The weighting factor for each subset's classifier vote is based on the sensitivity and specificity of the classifier developed in the training stage.

The anthropometric subsets were divided based on age, sex, BMI, Mallampati score, and neck circumference. Aging affects the female's voice by decreasing its pitch, and the male's voice by increasing its pitch (Torre III & Barlow, 2009). Furthermore, aging causes muscle mass loss, drying of the mucous membrane, and increasing speech variability (Linville, 2001); thus, two anthropometric subsets were used for age >50 and age <50 separately. Sex was selected as an anthropometric subset as it is known that females' voice has a higher fundamental frequency pitch than men (Titze, 2000), and that is independent of OSA severity; thus it is important to separately analyze males and females' breathing sounds. BMI has a significant effect on vocal quality and breathing sounds (Barsties et al., 2013); thus, two anthropometric subsets were used for BMI>35 and <35. Mallampati score is an indicator of pharyngeal size, and therefore associated with narrowing of upper airway (Gupta, Sharma, & Jain, 2005); thus, MpS>2 and <3 were chosen to form two anthropometric subsets. The neck circumference is one of the most important OSA risk factors (Ahbab et al., 2013); hence, participants with NC<40 and >40 were investigated separately. If the dataset's size was larger to enable more subjects in each subset, it might have been beneficial to form anthropometric subsets based on height and weight independent of BMI as well. Nevertheless, BMI and NC are highly correlated with weight and height; thus, including anthropometric subsets of weight and height may not be necessary to improve the accuracy significantly.

Among the anthropometric subsets, the lower age subset (age 50) showed the highest testing classification accuracy (86%) compared to the others. This was not a surprising outcome. Age is a well-known risk factor for OSA (Bixler, Vgontzas, Ten Have, Tyson, & Kales, 1998). Healthy individuals of age ≤50, in general, do not suffer from losing their upper airway muscle mass that in turn is responsible for upper airway collapse during an apnea/hypopnea event. They have more muscle tone than their age-matched OSA individuals. Thus, the loss of muscle tone is correlated with AHI in this group, and it affects breathing sounds significantly. In addition, after investigating the anthropometric information of the low age subset, it was found that the majority of non-OSA individuals in this subset also had BMI<35, MpS<3, NC<40, and were females. On the other hand, the majority of the OSA individuals in this subset were from the opposite categories. Therefore, the low age subset was expected to have the highest classification accuracy among the other subsets to classify individuals with AHI>15 and <15.

Another interesting observation for the selected feature combination for low age and male subsets is their high correlation (0.66 and 0.6, respectively) with AHI in the logarithm scale as shown in FIG. 11. This implies the severity of OSA increases exponentially with an increase in AHI. Clinically, this is also implied as the challenge in OSA diagnosis for people with relatively low AHI. Otherwise, a very high AHI matches with apparent clinical symptoms.

Figure 13:
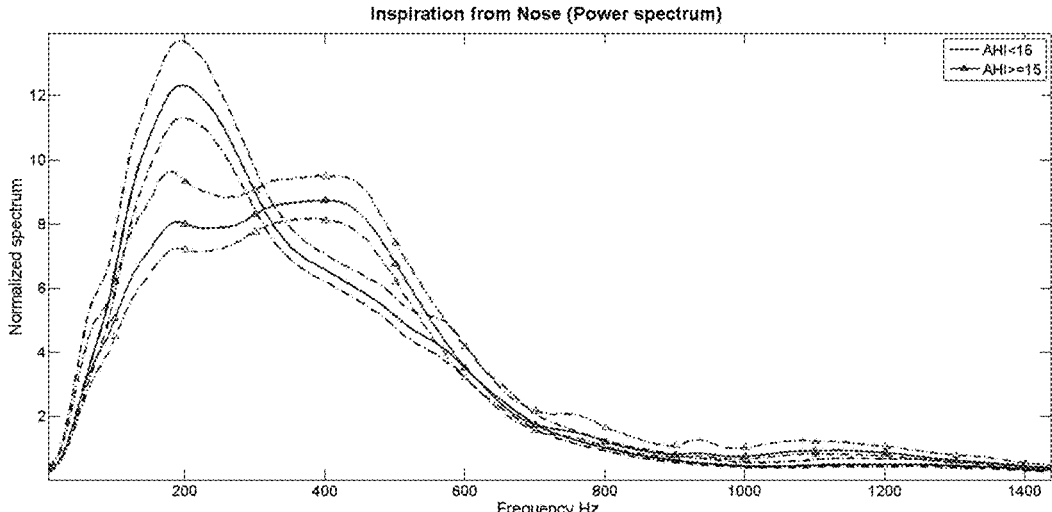
FIG. 13 shows, from the first experiment, average power spectrum of a signal recorded from nose inspiration, wherein the triangle-marked line set represents the OSA group, the unmarked line set represent the non-OSA group, and among both sets, the dotted lines represent the 95% confidence interval

Among the selected sound features, only 6 features were extracted from frequency components above 1100 Hz, while the rest of the features were extracted from frequency components below 600 Hz. This indicates that OSA affects low-frequency components the most. Thus, it is important to record breathing sounds with devices that do not filter out either low or high frequencies. One of the best sound features has been the mean of the slope of the power spectrum of the nose inspiratory signal recorded within a frequency band of 250-350 Hz. This feature was selected 3 times in the following subsets: age ≤50, Male, and MpS<3. During nose inspiration, the upper airway's muscles are active, while the pharynx cavity is patent. Pharynx cavity is responsible for transporting air from the nose to the lung, or the opposite. The upper airways of OSA individuals are commonly characterized by narrowing in the pharynx, thick tongue, losing muscles' tone, thick and long soft palate (Lan et al., 2006). These characteristics contribute to a significant narrowing of the upper airway cavity, increasing the chance of OSA during sleep. The mean of the spectral slope in 250-350 Hz shows that after 250 Hz the power of the sound of OSA individuals is increasing, but it is decreasing in non-OSA individuals (FIG. 13). It also shows the OSA individuals tend to have higher resonant frequencies than non-OSA individuals. These outcomes imply that the OSA group is characterized by a more deformed and stiffer upper airway than non-OSA. This is congruent with MRI/CT Imaging studies (Finkelstein et al., 2014; Lan et al., 2006) that showed the upper airway of OSA individuals during wakefulness on average had more regional compliance and stiffness.

Based on the final overall classification decisions (see FIG. 12), classifying a subject with an overall classification decision >0.7 or <−0.7 has about 90% confidence of being in the correct class. It was also investigated whether all the subsets' contribution to reach a reliable final vote for group assignment was significant. Excluding one of the selected subsets from the last voting stage degraded the overall classifier performance. Therefore, the proposed subsets were considered critical to the analysis in this experimentally supportive embodiment. It was of interest to note the anthropometric parameters of the misclassified subjects. As can be seen in Table 4, the majority of misclassified subjects in the non-OSA group have age <50, male-sex, BMI>35, NC>40, and MpS<3. On the other hand, the majority of misclassified subjects in the OSA group have age >50, male-sex, BMI<35, NC>40, and MpS<3; bold words show risk factors for the opposite group based on the STOP-BANG questionnaire. This implies the anthropometric parameters or risk factors show correlations with AHI, yet do not have classification power and can result in misclassification.

The forgoing results of Experiment A show that anthropometric parameters affect the tracheal breathing sounds, and their effects can be positively utilized to improve the accuracy and reliability of OSA identification during wakefulness. All selected sound features for each anthropometric subgroup were statistically significant different (p-value <0.05) between the two OSA groups (AHI≥15 & AHI<15). Despite using a sharp AHI threshold (AHI=15), the tested AWakeOSA algorithm showed a promising high classification blind-test accuracy with 82.1% sensitivity and 80.9% specificity. The AWakeOSA technology is thus anticipated to be of great interest for OSA identification during wakefulness, in particular for anesthesiologists to be prepared accordingly for patients undergoing full anesthesia. As such reliable and quick OSA identification will reduce the perioperative resources and cost significantly. It will also help in reducing the number of undiagnosed OSA and the need for PSG assessment; thus, reducing the healthcare cost significantly.

The simplified algorithm employed in Experiment A incorporates all features of FIGS. 1 through 4, except for inclusion of cranial features 202 (FIG. 3), but then jumps straight to step 412 (random forest classification) from steps 308 & 309, without intervening steps 401-411 & 413-501 of the more comprehensive embodiment that includes the entirety of FIGS. 4 through 6. The more comprehensive embodiment was the subject of Experiment B, discussed in more detail further below. After step 412, the data collection and classifier training process of the simplified embodiment of Experiment A jumps to an average weighted voting step for the final classification decision, like 502 of FIG. 6, and lacks the subsequent model combination step 503 since model-creation and model selection steps 401-411 are omitted in simplified variant.

In Experiment A, study participants (test subjects) were recruited randomly from those referred to the overnight PSG assessment at Misericordia Health Center (Winnipeg, Canada). The recording was performed about 1-2 hours prior to conducting the PSG study. During wakefulness and in the supine position (with the head rested on a pillow), tracheal breathing sound signals were recorded using a Sony microphone (ECM77B) embedded in a small chamber placed over the suprastemal notch of the trachea allowing ~2 mm space between the skin and the microphone. The participants were instructed to breathe deeply at the same flow rate, first, through their nose, and then, through their mouth with 5 breath cycles for each breathing maneuver. At the end of each breathing maneuver, participants were instructed to hold their breath for a few seconds to record the background noise (called silent period); more details about the recording protocol are available in the art (Elwali & Moussavi, 2017). The AHI values were extracted from the PSG records from Misericordia Health Center after the overnight PSG assessment that was prepared by a sleep technician.

Out of the 300 recorded breathing sounds, data of 199 individuals were selected as valid data. The criterion to include an individual's data was to have at least two clean (no artifacts, vocal noises, tones, interruptions, and low SNR) breathing cycles for each breathing maneuver. Each individual's sound signals were inspected by audio and visual means in time and frequency domains to separate the inspiratory and the expiratory phases. At the time of our wakefulness recordings, the first inspiratory phase was always marked to help to achieve a 100% accurate separation of the two phases. This initial dataset included data of 109 individuals with AHI<15 and 90 individuals with AHI>15. For simplicity, these two groups are referred to as non-OSA and OSA groups, hereafter. A block diagram representing the methodology of the simplified variant is presented in FIG. 14. Anthropometric information of the analyzed data (199 individuals) is presented in Table 1.

Overall, data of 113 individuals were used for training, and the remaining data of 86 individuals was used as the blind-test dataset. Within the training set, data of subjects with AHI≤10 (n=60) and AHI≥20 (n=40) were used for feature extraction for the two groups of the non-OSA and OSA (AHI<15 & AHI≥15), respectively; these data were from 100 subjects. Data of the remaining 13 subjects in the training dataset with 10<AHI<20 were not used for feature extraction but were included in the training classification process. Within the dataset of the 100 subjects used for training, the following anthropometric subsets were created: BMI<35, Age ≤50 and >50, Male, NC>40, and MpS≤2. These subsets had at least 30 and 20 individuals in each of the non-OSA and OSA groups, respectively.

Spectral and bispectral features were extracted from the breathing sounds data. The signals power spectra were calculated using the Welch method (Proakis, 2006), and their bispectra using the indirect class of conventional bispectrum estimator (Nikias & Raghuveer, 1987). Previously, (Elwali & Moussavi, 2017), it was found that the frequency band could be divided into main four discriminative frequency bands (i.e., 100-300 Hz, 350-600 Hz, 1000-1700 Hz, and 2100-2400 Hz). Using these four frequency bands, the spectral and bi-spectral features were extracted. Some of the features (i.e., mean, standard deviation, spectral entropy, skewness and kurtosis, spectral centroid, etc.) were extracted from the non-overlapping area between the average spectra/bispectra and their 95% confidence intervals of the two severity groups of the training dataset (AHI≥20 & AHI≤0). The minimum bandwidth to select a feature was set at 100 Hz. As an example, FIG. 13 shows the power spectra of the inspiratory nose breathing of the two severity groups (AHI≥20 & AHI≤10). Also calculated were Katz and Higuchi fractal dimensions (Higuchi, 1988; Katz, 1988), and Hurst exponent (Hurst, 1951) from the signals in the time domain. Therefore, for each subset, approximately 250 features were extracted from the time and frequency domains analyses of the mouth and nose breathing sound signals. All features were scaled into the range of [0, 1].

The p-value for each feature was calculated between the two OSA severity groups of the training dataset (AHI≥20 & AHI≤10) using the unpaired t-test. Any feature with a p-value >0.05 was excluded. Each feature was assigned a robustness score. At first, all features had robustness scores of zero. Using the available individuals of the two severity groups (AHI≥20 & AHI≤10), small groups of 15 per OSA seventy group was created. These groups were randomly generated and shuffled until all the individuals were selected at least once. All possible combinations of the small groups generated for each severity group were created. For each feature and using each combination, the p-value and normality check for each small group of the two severity groups (AHI≥20 & AHI≤10) were computed, separately; the Lilliefors test was used for normality check (Lilliefors, 1967). If the p-value was 0.05 and the normality check for each severity group (AHI≥20 & AHI≤10) was valid, the robustness score of this feature was increased by 1 point. This process was repeated 20 times. In the end, each feature had an overall robustness score. The features with an overall robustness score >0.6 of the maximum robustness score were selected for further analysis.

Using the available individuals' data of the two seventy groups (AHI≥20 & AHI≤10), and using a support vector machine classifier, the training accuracy, specificity, and sensitivity were computed for each feature in each anthropometric subset of the training dataset. All correlation coefficients between any two features were computed. Any set of features with in-between correlation coefficient were removed except the feature with the highest training classification accuracy, specificity, and sensitivity. The final set of features for each subset was selected by the end of this stage. The effect size of each of the selected features was also checked using Glass's delta equation (Glass, Smith, & McGaw, 1981). The selected features for each anthropometric subset were evaluated using a total training data of 113 individuals (62 with AHI<15, and 54 with AHI>15) and a blind testing dataset of the 86 individuals (47 with AHI<15, and 39 with AHI>15). Using the training data for each OSA severity group of each anthropometric subset separately, the outliers for each feature were removed, and the upper and lower adjacent values of boxplot were recorded (Benjamini, 1988; Tukey, 1977). Using the recorded values, the lowest lower adjacent value, and the highest upper adjacent value were recorded. Using the blind testing data, any value outside the recorded boundaries was removed.

Within each anthropometric subset, the selected features were combined to create three-feature and four-feature combinations. Using each combination and the training data, a Random-Forest (Breiman, 2001) classifier with ⅔ data in the bag (training) and ⅓ data out of the bag was used to evaluate the out-of-bag-validation testing accuracy, specificity, and sensitivity. The built-in function of Matlab (Breiman, 2001) was used. The Random-Forest routine included 1200 trees, interaction-curvature as a predictor selection, Gini's diversity index as split-criterion. A cost-matrix was used to compensate for the difference in the sample size between the two OSA severity groups of the initial dataset (AHI≥15 & AHI<15). This procedure was repeated three times. Therefore, for each feature combination, it resulted in three values for each of the accuracy, sensitivity, and specificity. All values were considered for the following stage, and the difference of the maximum and minimum of each three values were evaluated. The maximum difference for each of the accuracy, sensitivity, and specificity was recorded. For each feature combination, the average value of each of accuracy, sensitivity, and specificity was recorded. The feature combinations with values between the maximum average and the difference between the maximum average and the maximum difference or 2% were selected to be the best feature combinations.

Using the best feature combinations selected in the previous stage for each anthropometric subset separately, and using Random-Forest classifier with the same mentioned properties, the classification accuracies, sensitivities, and specificities of both the out of bag-validation and blind testing datasets were evaluated. This process was repeated five times; then, the average values were evaluated. For each anthropometric subset, the feature combinations with the highest validation and blind testing accuracies were selected as the best feature combinations for that subset. A random forest classifier is preferred over the previously used SVM classifier because 1) Breathing sound signals are stochastic signals, and the random forest has randomness in its nature, and 2) The OSA disorder has many confounding factors that affect breathing sounds and make it a heterogenous and complex condition. Therefore, in order to have multiple thresholds for each feature and thereby overcome the complexity and heterogeneity, a Random Forest classifier is preferably used.

For the final overall classification, the following steps were done with and without inclusion of anthropometric features with the sound features. The overall classification was evaluated using feature combinations which each combination was selected among the best for each subset. Different combinations were created due to having more than one final best feature combination per subset. The combination providing the highest overall classification accuracies, sensitivities, and specificities for both of out of bag-validation and blind testing datasets, was selected as the best feature combination. First, within each subset, the classification decision for each individual was evaluated; using assignment of 1 and −1 labels to each class (OSA and non-OSA groups). Using the outcomes of the subsets out-of-bag-validation, label 1 was multiplied by the sensitivity, and label −1 was multiplied by the specificity. After conducting the previous two steps on all subsets, the weighted classification decisions of each individual were averaged to result in the final classification decision; any value >0 or <0 was classified to OSA or non-OSA groups, respectively.

The misclassified individuals were investigated for any commonality between the OSA subjects misclassified to non-OSA, and/or the non-OSA subjects misclassified to OSA. The effect of neglecting a subset's results in the overall classification process was investigated. The correlation coefficient between AHI and anthropometric variables were investigated. Classifying the subjects using available variables of the STOP-BANG (i.e., Bang: BMI, age, NC, and gender) were conducted, then the classification accuracy, sensitivity, and specificity were evaluated. The correlation coefficient between AHI and the final selected sound features were investigated. Using the final selected feature combination for each subset, the correlation coefficients of the feature combination and AHI and its logarithm were evaluated.

Experiment B

Feature reduction and selection is a crucial stage for data analysis to reduce training time and overfitting, and to ease feature interpretation. Most of the popular feature reduction techniques rely on selecting features with high relevance to the response and minimum mutual information among one another. In this experiment, an improved algorithm embodying all steps of FIGS. 3 through 6 was used to reduce, select and model the most effective features for high classification results; the results were compared with five of the existing popular feature reduction and selection techniques. Using an adopted dataset from an obstructive sleep apnea study (113 participants as a training dataset, and 86 participants as a blind testing dataset), the operability of the improved algorithm was demonstrated. The features were preprocessed then modeled using three, four and five feature combinations. The models with a high correlation to the response and low overlap percentages were selected to be used in a Random Forest classification process. Then the models were combined to provide better accuracies. The resulted classification accuracies of using the improved algorithm were more than 25% higher than the results of using the five existing popular feature reduction selection techniques. In addition, the improved algorithm was about 20 times faster than the popular techniques. The improved technique can reduce and select the best sets of features for a high-performance classification process.

Features are the most important element in the classification process. Having irrelevant features would result in a useless classification process (a failure). Features should be extracted to have a relation with the response. Therefore, by combining these features in a model, it is possible to reconstruct the response (regression process) or reconstruct its main behavior (classification process). However, extracting many features would result in huge training times, lead to the curse of dimensionality, increase the overfitting, and make the interpretation hard on researchers and users. The improved algorithm reduces, selects, models, and utilizes the features to provide a better classification decision.

Having many features might indicates redundancy, and this redundancy might badly affect the generalization of the classification process. However, every relevant feature has a piece of information that might be important for a better classification process. But, increasing the number of features is not favorable, as mentioned before. Therefore, it is desirable to reduce the number of features while preserving all the important information for a successful classification process. Many studies and algorithms have been used to reduce the number of features by selecting the most relevant features to the response while reducing feature-redundancy (Battiti, 1994; Brown, 2009; Fleuret, 2004; Peng & Ding, 2005; Yang & Moody, 1999). That usually happens by selecting the features with the highest relevance to the response and the minimum mutual information. One prior example (Battiti, 1994) selects all the features that provide maximum mutual information with the response, while there is no selected feature which can be predicted by the other selected features. Another example (Yang & Moody, 1999) selects the features that together increase the joint mutual information about the response, and any feature with no added information is rejected. Yet another example (Peng & Ding, 2005) selects the features that maximally dependant on the response and maximally independent of each other.

The improved algorithm disclosed herein takes the features from the extraction stage to the final stage of the classification decision. This algorithm works only with numerical and ordinal responses. This algorithm takes the features to a modeling sequence (step 402) that revives the multi-feature interaction effect on the response. Then, it takes the models to a high correlation with response and variance reduction stages (steps 403-410), then to a classification stage (step 412) followed by model combination stage (step 501). The utility of the improved algorithm was demonstrated through a practical example of a dataset. This dataset belongs to participants (test subjects) with and without obstructive sleep apnea (OSA), a disorder that is characterized by repetitive episodes of complete (apnea) or partial (hypopnea) cessation of breath due to pharyngeal collapse, of which apnea-hypopnea index (AHI) is the OSA severity measurement.

The dataset of Experiment B was adopted from that of Experiment A (i.e., 199 participants). The recording was performed about 1-2 hours prior to conducting the Polysomnography (PSG) study; for more details on the recording protocol and the preprocessing stage, please see (Elwali & Moussavi, 2016). After their overnight PSG assessment analysis was completed by a sleep technician, the PSG study report of the study participants was obtained. Table 1 (from above) shows the anthropometric statistics of the 199 (83 females) study participants (subjects); the subject datasets were divided into two severity groups (AHI≥15 & AHI<15), training/validation (113 participants, 45 females) and blind testing (86 participants, 38 females).

Twenty-seven features (anthropometric and sound features) were adopted from Experiment A. The adopted features from Experiment A were characterized by the following: 1) They had a p-value <0.05 between individuals with AHI≥20 and AHI≤10. 2) They were normally distributed. 3) They had a low correlation between one another. 4) The outliers were removed; for more information about the selection methodology of the adopted features.

Five existing popular feature reduction techniques were used to reduce and select a set of three/four/five features, out of the 27 features, to be used in the classification process. The five feature reduction techniques are Mutual Information Maximization (MIM) (Brown 2009), Maximum-Relevance Minimum-Redundancy (MRMR) (Peng et al, 2005), Mutual Information-Based Feature Selection (MIFS) (Battiti, 1994), Joint Mutual Information (JMI) (Yang & Moody, 1999), and Conditional Mutual Information Maximization (CMIM) (Fleuret, 2004). For these techniques, use was made of Matlab™[2019] functions created by Stefan 2019. The selected sets were used in the validation and blind testing stages.

The methodology employed in Experiment B concerned the response nature and three main stages: linearization and model creation, feature reduction and selection technique, and model combination, as already described above with reference to FIGS. 5 and 6 of the illustrated embodiment, and thus not repeated here. Instead, attention is now turned to the experimental results. The initial dataset statistics of this study were already disclosed above in Table 1. The response (AHI) had a high positive skewness (1.73); therefore, the response was scaled by taking its logarithm. The new value for the skewness was –0.041, as shown in FIG. 15.

Directly reducing and selecting the sets of features using the five feature reduction techniques resulted in two three-feature combinations, two four-feature combinations, and four five-feature combinations; some combinations were repeated. Using these combinations in the classification process resulted in average validation and testing classification accuracies of 65.6% and 68.4%, sensitivities of 57.4% and 59%, and specificities of 72.8% and 76.3%, respectively; see Table 5 for more information.

TABLE 5

THE VALIDATION AND BLIND-TESTING
CLASSIFICATION ACCURACIES, SENSITIVITIES
AND SPECIFICITIES FOR THE DIRECTLY
SELECTED COMBINATIONS OF FEATURES
USING THE FIVE FEATURE REDUCTION/SELECTION
TECHNIQUES

| # of features/ | Used | Out of bag-validation | | |
|---|---|---|---|---|
| combination | technique | Accuracy | Sensitivity | Specificity |
| 3 | MIFS | 64.7% | 51.9% | 75.8% |
| 3 | Others | 67.7% | 60.6% | 73.8 |
| 4 | MIFS | 72.4% | 72.2% | 72.6% |
| 4 | Others | 60.1% | 50.9% | 68.1% |
| 5 | MIM | 62.1% | 48.1% | 74.2% |

TABLE 5-continued

THE VALIDATION AND BLIND-TESTING
CLASSIFICATION ACCURACIES, SENSITIVITIES
AND SPECIFICITIES FOR THE DIRECTLY
SELECTED COMBINATIONS OF FEATURES
USING THE FIVE FEATURE REDUCTION/SELECTION
TECHNIQUES

| | | | | |
|---|---|---|---|---|
| 5 | MRMR & CMIM | 67.2% | 59.3% | 74.2 |
| 5 | MIFS | 74.1% | 66.7% | 80.6% |
| 5 | JMI | 65.5% | 57.4% | 72.6% |

| # of features/ | Used | Blind testing | | |
|---|---|---|---|---|
| combination | technique | Accuracy | Sensitivity | Specificity |
| 3 | MIFS | 69.8% | 56.4% | 80.9% |
| 3 | Others | 67.7% | 61.5% | 72.9 |
| 4 | MIFS | 66.3% | 59% | 72.3% |
| 4 | Others | 66.3% | 53.2% | 77.1% |
| 5 | MIM | 70.9% | 61.5% | 78.7% |
| 5 | MRMR & CMIM | 73.3% | 61.5% | 83% |
| 5 | MIFS | 66.3% | 64.1% | 68.1% |
| 5 | JMI | 70.9% | 61.5% | 78.7% |

The average classification accuracies for the validation and blind testing datasets while using three-feature models were 71.5% and 66.3% for the inventive methodology of the illustrated embodiment of the present invention, 63.8% and 61.6% for MIM, 63.8% and 63.2% for MRMR, 64.2% and 64.7% for MI FS, 64.6% and 63.1% for JMI, and 67.1% and 65.2% for CMIM, respectively. The highest balanced (between validation and testing, and sensitivity and specificity, and above 60%) classification accuracies for the validation and blind testing datasets while using three-feature models are 73.2% and 73.8% for the inventive methodology, 74.3% and 74% for MIM, 71.3% and 74% for MRMR, 71.3% and 74% for MIFS, 72.3% and 74% for JMI, and 71.3% and 74% for CMIM, respectively. Using the five existing techniques, the selected model for all of them resulted in 74.3% and 74% validation and blind testing classification accuracies, respectively. The highest results (five per technique) using three-feature combination models are presented in Table 6; values in parenthesis represent the percentage of the used data.

TABLE 6

THE VALIDATION AND BLIND-TESTING CLASSIFICATION ACCURACIES,
SENSITIVITIES AND SPECIFICITIES FOR THE SELECTED THREE-FEATURE
MODELS; BOLD VALUES MEAN THAT THE MODEL HAS A BLIND TESTING
ACCURACY, SENSITIVITY AND SPECIFICITY MORE THAN 60%.

| Used | Out of bag-validation | | | Blind testing | | |
|---|---|---|---|---|---|---|
| technique | Accuracy | Sensitivity | Specificity | Accuracy | Sensitivity | Specificity |
| Proposed M1 | 77.2(98.2)% | 77.8% | 76.7% | 70.6(98.8)% | 71.1% | 70.2% |
| Proposed M2 | 73.2(96.5)% | 74.1% | 72.4% | 73.8(97.7)% | 64.9% | 80.9% |
| Proposed M3 | 80.4(88.5)% | 80% | 80.7% | 71.1(88.4)% | 65.6% | 75% |
| Proposed M4 | 71(86.7)% | 63.6% | 76.8% | 65.8(88.4)% | 61.1% | 70% |
| Proposed M5 | 73.7(85.8)% | 67.4% | 78.6% | 68.4(88.4)% | 59.4% | 75% |
| MIM | 69.5(91.2)% | 61.7% | 75.9% | 61.3(93)% | 59.5% | 62.8% |
| MIM, MRMR, MIFS, JMI | 68.7(99.1)% | 64.8% | 72.1% | 64(100)% | 66.7% | 61.7% |
| MIM, MRMR | 67(99.1)% | 64.8% | 68.9% | 62.8(100)% | 56.4% | 68.1% |
| MIM, MRMR, JMI, CMIM | 66.1(96.5)% | 62.7% | 68.9% | 72.3(96.5)% | 66.7% | 77.3% |
| All | 74.3(87.6)% | 70.5% | 77.2% | 74(89.5)% | 67.6% | 80.0% |
| MRMR | 69.6(96.5)% | 60.8% | 77% | 66.3(96.5)% | 56.4% | 75% |
| MIFS | 68(89.4)% | 57.8% | 75.9% | 68.4(88.4)% | 66.7% | 69.8% |
| MIFS | 70.3(95.6)% | 74.5% | 66.7% | 64.1(90.7)% | 56.8% | 70.7% |
| MIFS | 69.1(94.7)% | 69.4% | 68.9% | 74.4(95.3)% | 79.5% | 69.8% |
| JMI, CMIM | 67.3(94.7)% | 71.7% | 63.2% | 73.2(95.3)% | 65.8% | 79.5% |
| JMI | 77.1(93.8)% | 78.8% | 75.4% | 63.3(91.9)% | 62.9% | 63.6% |

TABLE 6-continued

THE VALIDATION AND BLIND-TESTING CLASSIFICATION ACCURACIES,
SENSITIVITIES AND SPECIFICITIES FOR THE SELECTED THREE-FEATURE
MODELS; BOLD VALUES MEAN THAT THE MODEL HAS A BLIND TESTING
ACCURACY, SENSITIVITY AND SPECIFICITY MORE THAN 60%.

| Used | Out of bag-validation | | | Blind testing | | |
|------|----------|-------------|-------------|----------|-------------|-------------|
| technique | Accuracy | Sensitivity | Specificity | Accuracy | Sensitivity | Specificity |
| CMIM | 77.1(93.8)% | 74.% | 80% | 67.1(95.3)% | 65.7% | 68.1% |
| CMIM | 76.9(92.9)% | 75% | 78.6% | 64.6(91.9)% | 65.7% | 63.6% |

M STANDS FOR MODEL

The average classification accuracies for the validation and blind testing datasets while using four-feature models were 75.7% and 69.6% for the inventive methodology, 68.6% and 65.6% for MIM, 71.2% and 67.1% for MRMR, 67.1% and 66.9% for MIFS, 71.6% and 65% for JMI, and 67.7% and 67.2% for CMIM, respectively. The highest balanced (between validation and testing, and sensitivity and specificity, and above 65%) classification accuracies for the validation and blind testing datasets while using four-feature models are 80% and 77.3% for the inventive methodology, 78.9% and 72.2% for MIM, 78.9% and 73.4% for MRMR, 72.3% and 71.4% for MIFS, 74.3% and 71.4% for JMI, and 70% and 71.3% for CMIM, respectively. Using the five techniques, the selected model for all of them resulted in 67.4% and 71.5% validation and blind testing classification accuracies, respectively. The highest results (five per technique) using four-feature combination models are presented in Table 7; values in parenthesis represent the percentage of the used data.

The average classification accuracies for the validation and blind testing datasets while using five-feature models were 81.2% and 71.3% for the inventive methodology, 74.7% and 66.6% for MIM, 76.3% and 67.4% for MRMR, 74% and 63.8% for MIFS, 75.9% and 67.7% for JMI, and 75.3% and 67.9% for CMIM, respectively. The highest balanced (between validation and testing, and sensitivity and specificity, and above 70%) classification accuracies for the validation and blind testing datasets while using five-feature models are 81.4% and 78.8% for the inventive methodology, 78.9% and 75.6% for MIM, 79.8% and 75.6% for MRMR, 78% and 75.6% for MIFS, 82.4% and 74.7% for JMI, and 83.3% and 74.7% for CMIM, respectively. Using the five techniques, the selected model for all of them resulted in 63.4% and 50% validation and blind testing classification accuracies, respectively. The highest results (five per technique) using five-feature combination models are presented in Table 8; values in parenthesis represent the percentage of the used data.

TABLE 7

THE VALIDATION AND BLIND-TESTING CLASSIFICATION ACCURACIES,
SENSITIVITIES AND SPECIFICITIES FOR THE SELECTED FOUR-FEATURE
MODELS; BOLD VALUES MEAN THAT THE MODEL HAS A BLIND TESTING
ACCURACY, SENSITIVITY AND SPECIFICITY MORE THAN 60%.

| Used | Out of bag-validation | | | Blind testing | | |
|------|----------|-------------|-------------|----------|-------------|-------------|
| technique | Accuracy | Sensitivity | Specificity | Accuracy | Sensitivity | Specificity |
| Proposed M1 | 77.8(85.8)% | 72.1% | 82.1% | 71.1(88.4)% | 68.8% | 72.7% |
| Proposed M2 | 80.0(86.7)% | 73.3% | 85.5% | 77.3(87.2)% | 77.4% | 77.3% |
| Proposed M3 | 76.4(94.7)% | 74.5% | 78% | 76.5(94.2)% | 81.6% | 72.1% |
| Proposed M4 | 70.9(94.7)% | 65.4% | 75.9% | 69.9(96.5)% | 71.1% | 68.9% |
| Proposed M5 | 77.3(84.1)% | 76.2% | 78.2% | 79.2(83.7)% | 77.4% | 80.5% |
| MIM | 72.5(93.8)% | 68.5% | 76.4% | 71.1(96.5)% | 70.3% | 71.7% |
| MIM, MRMR | 78.9(93.8)% | 79.6% | 78.2% | 72.2(91.9)% | 79.4% | 66.7% |
| MIM, MRMR | 75.2(93.8)% | 74.1% | 76.4% | 72.5(93)% | 65.7% | 77.8% |
| MIM, MRMR | 76.4(94.7)% | 79.6% | 73.2% | 69.9(96.5)% | 64.9% | 73.9% |
| MIM | 75.2(93.8)% | 74.1% | 76.4% | 68.8(93)% | 63.6% | 72.3% |
| MRMR | 78.2(94.7)% | 79.6% | 76.8% | 70(93)% | 71.4% | 68.9% |
| MRMR, MIFS, JMI | 72.3(87.6)% | 75% | 70.2% | 71.4(89.5)% | 70.3% | 72.5% |
| MIFS, JMI | 67(96.5)% | 62.7% | 70.5% | 71.1(96.5)% | 64.1% | 77.3% |
| MIFS | 65.8(95.6)% | 61.5% | 69.5% | 71.6(94.2)% | 63.2% | 79.1% |
| MIFS, CMIM | 69.4(95.6)% | 67.3% | 71.2% | 73.8(93)% | 59.5% | 86% |
| MIFS, CMIM | 76.6(95.6)% | 76.5% | 76.7% | 70.2(97.7)% | 61.5% | 77.8% |
| JMI | 65.8(95.6)% | 72.2% | 59.6% | 70(93)% | 77.8% | 63.6% |
| JMI | 81.5(92.9)% | 81.1% | 81.8% | 69.1(94.2)% | 63.9% | 73.3% |
| JMI | 69.2(92)% | 70.6% | 67.9% | 66.2(89.5)% | 57.1% | 73.8% |
| CMIM | 70(94.7)% | 65.4% | 74.1% | 71.3(93)% | 64.9% | 76.7% |
| CMIM | 73(99.1)% | 70.4% | 75.4% | 67.9(97.7)% | 59.5% | 74.5% |
| CMIM | 69.4(95.6)% | 65.4% | 72.9% | 70(93)% | 59.5% | 79.1% |

M STANDS FOR MODEL.

TABLE 8

THE VALIDATION AND BLIND-TESTING CLASSIFICATION ACCURACIES,
SENSITIVITIES AND SPECIFICITIES FOR THE SELECTED FIVE-FEATURE
MODELS; BOLD VALUES MEAN THAT THE MODEL HAS A BLIND TESTING
ACCURACY, SENSITIVITY AND SPECIFICITY MORE THAN 60%.

| Used | Out of bag-validation | | | Blind testing | | |
|------|----------|-------------|-------------|----------|-------------|-------------|
| technique | Accuracy | Sensitivity | Specificity | Accuracy | Sensitivity | Specificity |
| Proposed M1 | 77.1(93.8)% | 76.9% | 77.2% | 77.4(97.7)% | 86.5% | 70.2% |
| Proposed M2 | 76.6(95.6)% | 72.2% | 80.7% | 78.3(96.5)% | 75.7% | 80.4% |
| Proposed M3 | 81.6(85)% | 75% | 87% | 77.3(87.2)% | 71% | 81.8% |
| Proposed M4 | 81.4(75.2)% | 71.4% | 88.2% | 78.8(76.7)% | 72.4% | 83.8% |
| Proposed M5 | 86(92)% | 84.3% | 87.5% | 76.3(93)% | 80.6% | 72.7% |
| MIM, MRMR | 75.5(91.2)% | 75.9% | 75% | 74.4(90.7)% | 69.7% | 77.8% |
| MIM, MRMR | 73.8(92)% | 74.1% | 73.6% | 70.4(94.2)% | 68.6% | 71.7% |
| MIM | 80(94.7)% | 77.8% | 82.1% | 70.9(91.9)% | 64.7% | 75.6% |
| MIM | 77.3(94.7)% | 75.9% | 78.6% | 75(93)% | 85.3% | 67.4% |
| MIM, MRMR, MIFS | 78.9(93.8)% | 81.5% | 76.4% | 75.6(90.7)% | 73.5% | 77.3% |
| MRMR | 77.1(93.8)% | 75.9% | 78.2% | 71.6(94.2)% | 62.9% | 78.3% |
| MRMR, MIFS | 73.3(87.6)% | 65.9% | 78.9% | 75.3(89.5)% | 67.6% | 82.5% |
| MIFS | 74.5(85)% | 66.7% | 81.1% | 71.6(86)% | 63.3% | 77.3% |
| MIFS | 73.1(92.9)% | 68.5% | 77.8% | 67.9(94.2)% | 65.7% | 69.6% |
| MIFS | 76.9(92.9)% | 77.8% | 75.9% | 70.4(94.2)% | 62.9% | 76.1% |
| JMI, CMIM | 82.4(92.9)% | 83.3% | 81.5% | 74.7(91.9)% | 79.4% | 71.1% |
| JMI, CMIM | 80.9(94.7)% | 79.6% | 82.1% | 70.9(91.9)% | 68.6% | 72.7% |
| JMI, CMIM | 80(94.7)% | 81.5% | 78.6% | 70.7(95.3)% | 70.3% | 71.1% |
| JMI, CMIM | 84.1(92)% | 79.6% | 88.7% | 72.7(89.5)% | 68.8% | 75.6% |
| JMI, CMIM | 79.4(92)% | 81.5% | 77.4% | 73.8(93)% | 72.7% | 74.5% |

M STANDS FOR MODEL.

Using three-feature per model (2925 models), the average time to execute each of the procedures for finding the best 20 models were 8 and 155.4 seconds for the inventive method and one of the popular reduction technique, respectively. Using four-feature per model (17550 models), the average time to execute each of the procedures for finding the best 20 models were 46.7 and 937.2 seconds for the inventive method and one of the popular reduction technique, respectively. Using five-feature per model (80730 models), the average times to execute each of the procedures for finding the best 20 models were 269.6 and 4464 seconds for the inventive method and one of the popular reduction technique, respectively; therefore, the inventive method was ~20 times faster than any of the five popular methods.

Combining models enhanced the classification results and covered more participants. Using three-feature model combinations resulted in maximum accuracies of 78.4 and 76.5% for the validation and blind testing datasets, respectively, and covered 98.5% of the dataset. Using four-feature model combinations resulted in maximum accuracies of 79.3 and 81.1% for the validation and blind testing datasets, respectively, and covered 98.5% of the dataset. Using five-feature model combinations resulted in maximum accuracies of 88.2 and 83.5% for the validation and blind testing datasets, respectively, and covered 98% of the dataset; see Table 9 for the results.

TABLE 9

THE VALIDATION AND BLIND-TESTING CLASSIFICATION ACCURACIES,
SENSITIVITIES AND SPECIFICITIES FOR THE COMBINATIONS OF MODELS;
BOLD VALUES REPRESENT THE RESULTS OF THE BEST MODELS.

| Combination | Out of bag-validation | | | Blind testing | | |
|-------------|----------|-------------|-------------|----------|-------------|-------------|
| | Accuracy | Sensitivity | Specificity | Accuracy | Sensitivity | Specificity |
| Three-feature model combination | | | | | | |
| M2-M3-M4 | 75.7(98.5)% | 68.6% | 81.7% | 74.1(98.5)% | 68.4% | 78.7% |
| M2-M3-M5 | 78.4(98.5)% | 70.6% | 85% | 76.5(98.5)% | 73.7% | 78.7% |
| Four-feature model combination | | | | | | |
| M1-M3-M5 | 78.4(98.5)% | 68.6% | 86.7% | 80(98.5)% | 76.3% | 82.3% |
| M2-M3-M5 | 79.3(98.5)% | 70.6% | 86.7% | 81.2(98.5)% | 73.7% | 87.2% |
| M2-M4-M5 | 80.2(98)% | 70.6% | 88.3% | 79.8(98)% | 73.7% | 84.8% |
| Five-feature model combination | | | | | | |
| M1-M3-M4 | 86.1(96.5)% | 78.4% | 93% | 81(96.5)% | 78.4% | 83% |
| M1-M4-M5 | 83.6(98)% | 78.4% | 88.1% | 82.4(98)% | 81.6% | 83% |
| M2-M3-M4 | 85.2(96.5)% | 78.4% | 91.2% | 83.3(96.5)% | 81.1% | 85.1% |
| M2-M4-M5 | 88.2(98)% | 82.4% | 93.2% | 83.5(98)% | 81.6% | 85.1% |

M STANDS FOR MODEL.

Any classification process relies on a set of features, and these features have a relation with the response. On many occasions, the number of extracted features is enormous, and some of these features might be inefficient, redundant, and might cause overfilling. In addition, as the number of features increases, the computational cost increases. Therefore, reducing the number of features is a crucial stage to find the best set of features, in a short time, which can provide a high classification accuracy as well as a sense of generalization.

After extracting the features, and applying basic feature reduction techniques, one might end up with many features that can construct many sets of features; therefore, it is desirable to select the best set of features. In Experiment B, 182 features were extracted from the dataset, and after applying the basic feature reduction techniques, 27 different significant features resulted. Now, it is desirable to select the best and final set of features (e.g., three, four, five . . . features), but it is time-consuming to try all the combinations (27C3, 4, 5, . . . ); hence the inclusion of the novel feature-combination selection in preferred embodiments of the inventive algorithm.

Using the five aforementioned feature selection techniques, which involved in selecting the set of features with the high relevance to the response and low redundancy between one another, the classification accuracies were poor for both the validation and blind testing datasets while using three, four and five features per combination. Also, increasing the number of features did not enhance the classification process. Therefore, directly using the features in algorithmic modeling (random forest classifier) was not the best approach for the classification process. For this reason, the preferred embodiment of the disclosed invention models the response using the available features, then uses a machine learning algorithm together with the created model to get the best classification decisions. The created models considered modeling the relation between the features-interactions and the response in a linear relationship. In addition, to have a better model to represent the response, the skewness of the response distribution should be low hence the aforementioned scaling of the response. With reference to FIG. 16, the resulted models showed promising results for representing and predicting the response.

By scaling the response and building the models, the response of the five-feature reduction and selection techniques were better than directly using the features, as seen in Tables 5, 6, 7, and 8. But, such approach consumed a lot of time, and the classification percentages were overall lower than the results of the novel technique. In the inventive technique, all the possible models were computed, then the ones with the highest correlation with the response were selected. Here, reliance was not made on the overall correlation, because it might neglect any opposite correlation in the in-between segments. This ensured linearity throughout the dataset. The disclosed algorithm only works on the response that has a severity sense (numerical or ordinal variables).

Having a high correlation does not ensure no or low sparsity of participants (misclassifications) around the midline between the actual and predicted response. Therefore, efforts were made to search for the model with the minimum variance around the linear line between the response and prediction from two perspectives. This was done by reducing the subject overlap percentage between the segments from the response and prediction perspectives, which ensured selection of a model with high linearity and low sparsity around the midline.

The numerical or ordinal variables technique also dealt with missing data by performing weighted majority voting in order to involve most of the available participants in the dataset. The proposed methodology was more effective, accurate, and faster than using the five aforementioned existing techniques, as shown in Table 9. This demonstrates promising results from the inventive algorithm that can reduce the features, provide better representation, reduce the computational cost (during the selection and classification), and enhance the classification accuracy.

Microphone Coupler

The spectral features of respiratory sounds offer a wealth of information regarding airflow and pathology of the upper airway. Tracheal and other respiratory sounds are commonly recorded by means of a microphone or accelerometer affixed on the surface of the skin [1, 2]. When using a microphone, a volume of air between the surface of the skin and the sensing element of the microphone is required to convert upper airway or chest wall vibrations into sound pressure which is measurable by the microphone [3]. A fixture known as a microphone coupler is used to both allow a means of attaching the microphone to the skin and, by creating a cavity in the microphone coupler (defined as an air-chamber), creates a sealed pocket of air between the microphone sensing element and skin surface. An appropriate air-chamber design is critical to ensure the optimal signal is being received by the microphone. New microphone hardware was developed based on re-visitation of a prior design of the air-chamber and coupler; the results of which are summarized below.

The microphone coupler with air-chamber must be designed to accommodate the microphone to be used so as the microphone is held securely and so the microphone benefits from the effect of the air-chamber. Applied design criteria for the coupler with its air-chamber were two-fold: 1) the coupler should permit easy and secure attachment to the skin and should also act to position the sensing element of the microphone correctly with the base of the air-chamber, and 2) the effect of the air-chamber should benefit the recorded signal by permitting the full frequency range of the microphone while having the desired effects of optimal sensitivity at a relatively wide (>5 kHz) frequency range for sound collection.

The novel coupler was custom-designed and manufactured from a single, solid piece of ultra-high-molecular-weight polyethylene (UHMWPE). The air-chamber was cut into the front surface of the coupler, whereas on the backside a counter-bore hole was cut to mount and position the microphone correctly with the base of the air-chamber. In addition, the flat surface on the front of the coupler surrounding the air-chamber was designed to accommodate double-sided adhesive discs (Manufacturer: 3M, Product Number: 2181) which provide excellent adhesion for secure attachment to the skin.

The geometry of the air-chamber was chosen as conical since conical air-chambers have been proven to provide 5-10 dB more sensitivity than cylindrical air-chambers of the same diameter [9]. The design of the conical air-chamber was then divided into three basic dimensional properties: (i) Diameter at the bottom of the air-chamber (i.e. at the microphone capsule. (ii) Diameter at the top of the air-chamber (i.e. at the surface to be in contact with the skin). (iii) Depth of the air-chamber.

Figure 17:
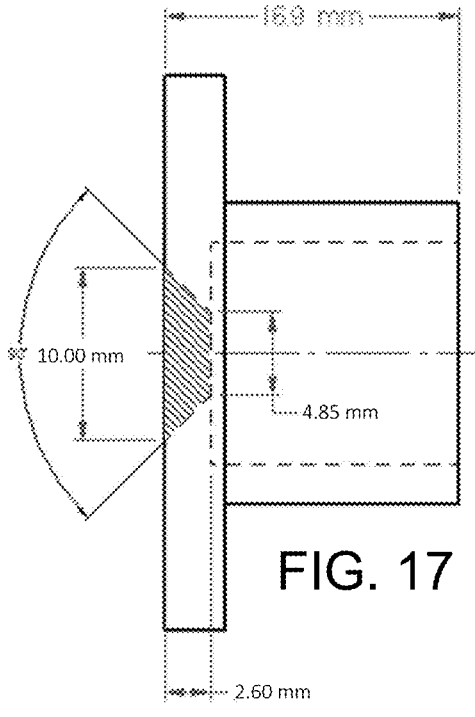
FIG. 17 is a schematic cross-sectional view of a microphone coupler having an air chamber (identified by hatching) particularly suited for the audio recording procedure of FIG. 2.

The diameter at the bottom of the air-chamber was selected as 4.85 mm. This dimension was chosen to allow full exposure of the entry ports to the microphone without obstruction. The diameter at the top of the air-chamber and depth of the air-chamber design were established using the recommendations within the literature, following the principals that overall high-frequency response decreases with increasing air-chamber depth [3] and the optimal air-chamber opening diameter is between 10 and 15 mm [9]. Air-chambers were made with diameters at the top of the air-chamber of 10.00 mm (FIG. 17), 12.50 mm, and 15.00 mm. The depth of the air-chamber was selected as 2.60 mm.

The three microphone coupler designs described above placed the microphone capsule in direct contact with the UHMWPE material of the coupler. Our second revision to the microphone coupler design incorporates a slightly larger counter-bore hole to accommodate a rubber isolator ring (material thickness of 1.50 mm) around the perimeter of the capsule of the microphone. Using the isolator ring, the metal body of the microphone capsule is no longer in direct contact with the UHMWPE material of the coupler. With particular focus on examining higher frequency components, it was chosen to test the addition of the isolator ring with the 10.00 mm chamber as that chamber showed the most optimal response between approximately 150-10,000 Hz for inspiration and 130-8,500 Hz for expiration. The same signal was applied to the air-chambers with and without the isolator ring, and responses were compared.

An AOM-5024L-HD-R electret condenser microphone was used because of its high fidelity over the frequency range of respiratory sounds. This microphone was used to test the various designs for the air-chambers and couplers described herein. The selected microphone had cylindrical dimensions of 9.7 mm in diameter and 5.0 mm in height, a signal-to-noise ratio of 80 dB (1 kHz, 94 dB input, A-weighted), frequency range of 20-20,000 Hz, and omni-directional directivity.

The microphone was connected using the recommended drive circuit described in the datasheet using component values of 2.2 kΩ and 0.1 µF for the resistor and capacitor, respectively. Digitization of the analog signal from the microphone was performed using custom-designed hardware consisting of a SGTL5000 stereo codec (Fe-Pi Audio Z v2), ARM1176JZF-S processor (Raspberry Pi Zero W), and precision regulated power supply (custom design). Auditory information was stored in the lossless .WAV style file format at a sampling rate of 44,100 Hz with 16-bit precision. Audio recordings were performed by affixing the microphone coupler (with attached microphone) to the skin using double-sided adhesive rings. For each recording, the air-chamber and microphone were positioned over the suprasternal notch of the trachea after it was cleaned by isopropyl alcohol; a new adhesive ring was used each time the coupler was replaced.

All recordings were completed in an anechoic chamber (>30 dB noise reduction). The identical recording device hardware on the same human subject was used for each recording. For each recording, the subject was guided by the researcher to follow a breathing pattern of 5 complete breathing cycles at their normal flow rate starting with inspiration and breathing exclusively through the mouth; they were also instructed to hold their breath for 5 sec. at the end of the 5 breathing cycles.

The recorded data was pre-processed and normalized using the procedure mentioned in previous work [6, 8]. First, each recording was manually investigated in the time-frequency domain to exclude breathing phases including artifacts, vocal noises, tones, interruption or very low signal-to-noise ratio compared to the background noise (evaluated during the breath-hold segment). Next, breathing sounds were filtered with a band-pass (75-20000 Hz) filter (Butterworth) of 4$^{th}$ order. Lastly, each respiratory phase signal was normalized to its energy to remove the effect of plausible airflow fluctuation between the breathing cycles [8]. The power spectra of the normalized data were then estimated using the Welch method with a window size of 1024 samples (~23.22 ms) and 50% overlap between the adjacent windows. The average power spectrum was evaluated for each respiratory phase (inspiration or expiration) and varying diameter at the opening of the air-chamber.

Figure 18:
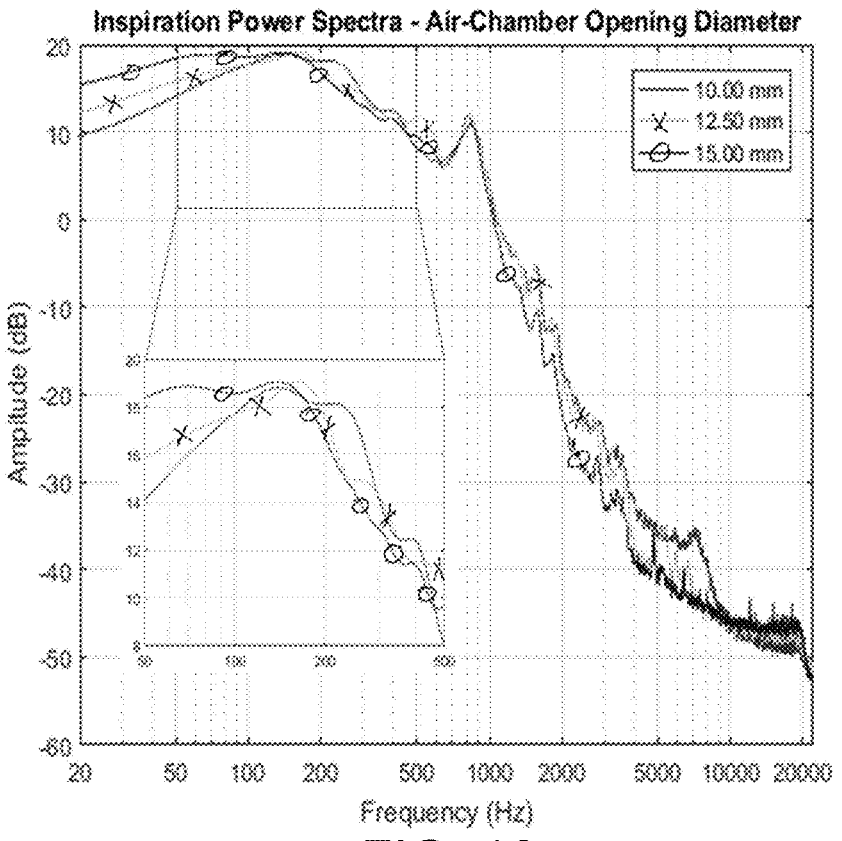
FIG. 18 shows microphone air-chamber response during inspiration for different air-chamber dimensions of the microphone coupler of FIG. 17, and includes an enlarged inset showing response curves from 50-500 Hz.

During inspiration (FIG. 18), the 15.00 mm chamber provides the better (higher amplitude) response below approximately 150 Hz. Between approximately 150-430 Hz, the 10.00 mm chamber was observed to provide optimal response until the 12.50 mm chamber dominates for the small range between approximately 430-640 Hz. From 640-815 Hz, the 12.50 mm chamber provided the slightly optimal response with the 10.00 mm chamber showing a near equal response. From 815 Hz through until approximately 3750 Hz, the 10.00 mm and 12.50 mm chambers continued to exhibit a similar response, with both chambers clearly performing better than the 15.00 mm chamber. From approximately 3750-10,000 Hz, the 10.00 mm chamber provided a significantly better response than either the 12.50 mm or 15.00 mm chambers. After 10 kHz, the 15.00 mm chamber showed the optimal response though the signal was quite low amplitude and noisy in this frequency range.

For the expiratory signals (FIG. 19), much of the same trend was seen as observed from the inspiratory signals with slight difference: below approximately 130 Hz, the 15.00 mm chamber provided the best response of the three chambers. Between the ranges of approximately 130-220 Hz, 300-340 Hz, and 450-580 Hz, the 12.50 mm chamber provided optimal response however the 15.00 mm chamber dominated with the better response for the small range between approximately 220-300 Hz and the 10.00 mm chamber dominated the response between approximately 340-450 Hz. From 580-2500 Hz, the 10.00 mm chamber provided the best response, with the 15.00 mm chamber dominating in the small range from 2500-2800 Hz, and then the 10.00 mm chamber having the noticeably better response through until approximately 3700 Hz when the response curves of the 10.00 mm and 15.00 mm chambers become quite similar. After approximately 8500 Hz, a prominent shift is noted where both the 12.50 mm and 15.00 mm chambers provided better response as compared to the 10.00 mm chamber; though once again it was noted that the signal is very low amplitude and noisy in this region.

Figures 19, 20:
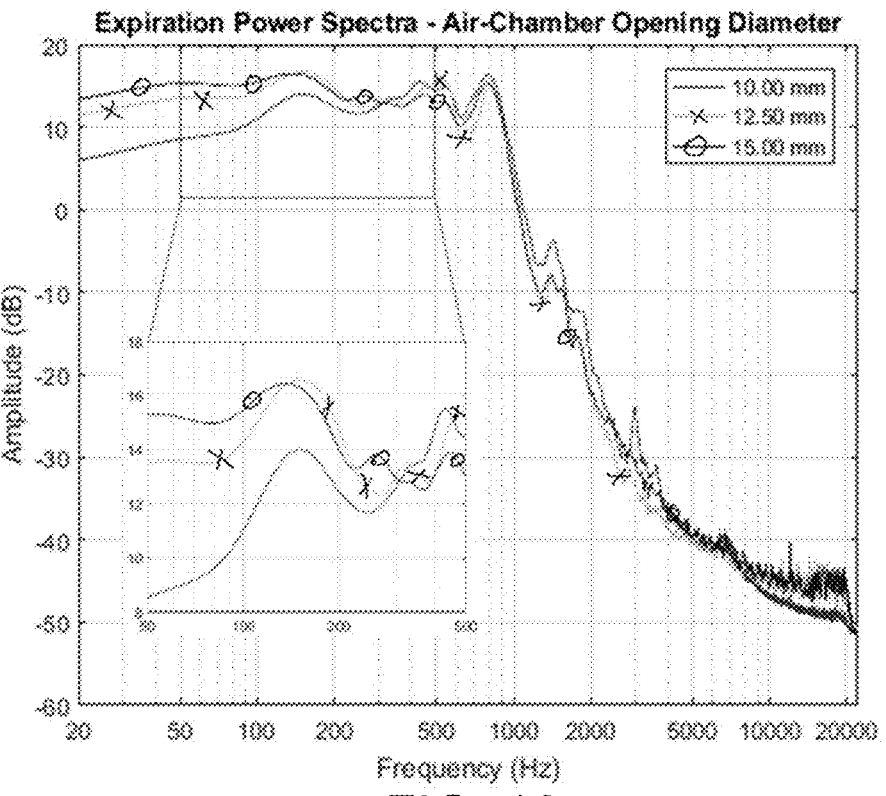
FIG. 19 shows microphone air-chamber response during expiration for the different air-chamber dimensions of the microphone coupler of FIG. 17, and includes an enlarged inset showing response curves from 50-500 Hz.
FIG. 20 shows microphone air-chamber response for a 10.00 mm air chamber diameter during inspiration and expiration, and illustrates the effects of inclusion or omission of a rubber isolator ring.

FIG. 20 shows the response curves for the 10.00 mm air-chamber with and without the addition of the rubber isolator ring around the perimeter of the microphone during inspiration and expiration. During inspiration, from approximately 40-200 Hz, the air-chamber without the insulator provided better response. Between approximately 200-890 Hz, the rubber insulator provided better response; however, past 890 Hz, the chamber without the insulator provided a marginally better response. During expiration, below approximately 430 Hz, the air-chamber without the insulator provides better response. Between approximately 430-820 Hz, the rubber insulator provides better response; however, past 820 Hz, it was observed the better response was achieved without the insulator.

The power spectra for inspiration and expiration respiratory phases provided a clear difference regarding the optimal air-chamber as a function of frequency, i.e. <150 Hz, 150-10,000 Hz, and >10,000 Hz for inspiration and <130 Hz, 130-8,500 Hz, and >8,500 Hz for expiration. These differences can be explained by several physical properties of the air-chamber.

Firstly, acoustic resonance as a function of the geometry of the air-chamber acts to increase the sound pressure for frequencies near to the natural frequency of each respective air-chamber. Calculations indicate the effect of resonance can act to amplify the sound pressure up to approximately 3 times for frequencies close to 0 Hz; the effect decays exponentially up to approximately 150 Hz, after which resonance has little to no effect. The spectra captured for frequencies <150 Hz and <130 Hz (for inspiration and expiration phases, respectively) are believed to be attributed to the effects of resonance as a function of air-chamber geometry.

Secondly, air-chambers with larger opening diameter suffer from increased surface area which acts to a larger extent to absorb sound; thus decreasing sound pressure reaching the microphone. Calculations indicate an acoustic impedance for the air-chamber of smallest opening more than 2× greater than that of the air-chamber with the largest opening. The higher the acoustic impedance of the chamber, the less sound is absorbed into the material. With the effects of resonance not present in frequencies >150 Hz and >130 Hz (for inspiration and expiration phases, respectively), the effect of acoustic impedance as a function of air-chamber surface area can explain the results seen in the mid-range, i.e. between 150-10,000 Hz for inspiration and 130-8,500 Hz for expiration.

Conversely, air-chambers of larger opening do have the benefit of capturing a larger area of surface vibration (at the skin), which has the overall effect of capturing a larger extent of the sound compared to the air-chambers of smaller opening. For the range of frequencies above 10,000 Hz and 8500 Hz (for inspiration and expiration phases, respectively), it is this phenomenon of increased sound capture that is believed to dominate the effect of acoustic impedance and make the air-chamber of largest opening the optimal choice.

Finally, since mechanical vibrations on the capsule of the microphone may translate to vibrations in the diaphragm of the microphone, the rubber isolator ring provides a benefit irrespective of the properties of the air-chamber by damping any vibrations that are transmitted through the material of the microphone coupler.

In general, the air-chambers of smaller opening performed better at frequencies in the range of 150-10,000 Hz for inspiration and 130-8,500 Hz for expiration. For frequencies above and below the respective ranges, the chamber of largest opening provided the optimal sensitivity. The addition of the rubber isolator ring proved beneficial to increase the sensitivity of the 10.00 mm chamber for the frequency range of approximately 200-890 Hz for inspiration, and similarly in 430-820 Hz range for expiration. Given that many precursory recording systems presented in literature have an upper limit of 5 kHz, it is recommended that the air-chamber of smaller opening diameter be utilized unless analysis of frequencies less than approximately 150 Hz or 130 Hz (for inspiration and expiration, respectively) is the focus. As well, the use of a rubber-isolator may prove beneficial dependent upon the frequency range being studied.

It will be appreciated that though the forgoing describes particular microphone air-chambers optimized for use in the OSA screening context of the present invention, other microphone designs may alternatively be used. Likewise, since various modifications can be made relative to the preferred embodiments described herein above, and many apparently widely different embodiments thereby achieved, it is intended that all matter contained in the accompanying specification shall be interpreted as illustrative only and not in a limiting sense.

REFERENCES

AwakeOSA—Experiment A
Ahbab, S., Ataoglu, H. E., Tuna, M., Karasulu, L., Cetin, F., Temiz, L. U., & Yenigun, M. (2013). Neck circumference, metabolic syndrome and obstructive sleep apnea syndrome; evaluation of possible linkage. *Medical Science Monitor: International Medical Journal of Experimental and Clinical Research,* 19, 111-117. doi: 10.12659/MSM.883776 [doi]
American Academy of Sleep Medicine. (2005). *International classification of sleep disorders: Diagnostic and coding manual* (2nd ed.). Westchester: American Academy of Sleep Medicine.
American Society of Anesthesiologists. (2006). Practice guidelines for the perioperative management of patients with obstructive sleep apnea: A report by the american society of anesthesiologists task force on perioperative management of patients with obstructive sleep apnea. *Anesthesiology,* 104(5), 1081. doi: 00000542-200605000-00026 [pii]
Barsties, B., Verfaillie, R., Roy, N., & Maryn, Y. (2013). Do body mass index and fat volume influence vocal quality, phonatory range, and aerodynamics in females? Paper presented at the *CoDAS,* 25(4) 310-318.
Benjamini, Y. (1988). Opening the box of a boxplot. *The American Statistician,* 42(4), 257-262.
Bixler, E. O., Vgontzas, A. N., Ten Have, T., Tyson, K., & Kales, A. (1998). Effects of age on sleep apnea in men: I. prevalence and severity. *American Journal of Respiratory and Critical Care Medicine,* 157(1), 144-148.
Bonsignore, M. R., Baiamonte, P., Mazzuca, E., Castrogiovanni, A., & Marrone, O. (2019). Obstructive sleep apnea and comorbidities: A dangerous liaison. *Multidisciplinary Respiratory Medicine,* 14(1), 8.
Breiman, L. (2001). Random forests. *Machine Learning,* 45(1), 5-32.
Chung, F., & Elsaid, H. (2009). Screening for obstructive sleep apnea before surgery: Why is it important? *Current Opinion in Anaesthesiology,* 22(3), 405-411. doi: 10.1097/ACO.0b013e32832a96e2 [doi]
El-Sayed, I. H. (2012). Comparison of four sleep questionnaires for screening obstructive sleep apnea. *Egyptian Journal of Chest Diseases and Tuberculosis,* 61(4), 433-441.
Elwali, A., & Moussavi, Z. (2017). Obstructive sleep apnea screening and airway structure characterization during wakefulness using tracheal breathing sounds. *Annals of Biomedical Engineering,* 45(3), 839-850.
Epstein, L. J., Kristo, D., Strollo, P. J., Jr, Friedman, N., Malhotra, A., Patil, S. P., . . . Adult Obstructive Sleep Apnea Task Force of the American Academy of Sleep Medicine. (2009). Clinical guideline for the evaluation, management and long-term care of obstructive sleep apnea in adults. *Journal of Clinical Sleep Medicine: JCSM: Official Publication of the American Academy of Sleep Medicine,* 5(3), 263-276.
Finkelstein, Y., Wolf, L., Nachmani, A., Lipowezky, U., Rub, M., & Berger, G. (2014). Velopharyngeal anatomy in patients with obstructive sleep apnea versus normal subjects. *Journal of Oral and Maxillofacial Surgery,* 72(7), 1350-1372.

Glass, G. V., Smith, M. L., & McGaw, B. (1981). *Meta-analysis in social research* Sage Publications, Incorporated.

Goldshtein, E., Tarasiuk, A., & Zigel, Y. (2011). Automatic detection of obstructive sleep apnea using speech signals. *Biomedical Engineering, IEEE Transactions On,* 58(5), 1373-1382.

Gross, J. B., Apfelbaum, J. L., Caplan, R. A., Connis, R. T., Cote, C. J., Nickinovich, D. G., . . . Ydens, L. (2014). Practice guidelines for the perioperative management of patients with obstructive sleep apnea an updated report by the american society of anesthesiologists task force on perioperative management of patients with obstructive sleep apnea. *Anesthesiology,* 120(2), 268-286.

Gupta, S., Sharma, R., & Jain, D. (2005). Airway assessment: Predictors of difficult airway. *Indian J Anaesth,* 49(4), 257-262.

Higuchi, T. (1988). Approach to an irregular time series on the basis of the fractal theory. *Physica D: Nonlinear Phenomena,* 31(2), 277-283.

Hurst, H. E. (1951). Long-term storage capacity of reservoirs. *Trans. Amer. Soc. Civil Eng.,* 116, 770-808.

Jung, D. G., Cho, H. Y., Grunstein, R. R., & Yee, B. (2004). Predictive value of kushida index and acoustic pharyngometry for the evaluation of upper airway in subjects with or without obstructive sleep apnea. *Journal of Korean Medical Science,* 19(5), 662-667. doi: 200410662 [pii]

Karimi, D. (2012). *Spectral and bispectral analysis of awake breathing sounds for obstructive sleep apnea diagnosis* (MSc).

Katz, M. J. (1988). Fractals and the analysis of waveforms. *Computers in Biology and Medicine,* 18(3), 145-156.

Kriboy, M., Tarasiuk, A., & Zigel, Y. (2014). Detection of obstructive sleep apnea in awake subjects by exploiting body posture effects on the speech signal. Paper presented at the *Engineering in Medicine and Biology Society (EMBC),* 2014 36th Annual International Conference of the IEEE, 4224-4227.

Lan, Z., Itoi, A., Takashima, M., Oda, M., & Tomoda, K. (2006). Difference of pharyngeal morphology and mechanical property between OSAHS patients and normal subjects. *Auris Nasus Larynx,* 33(4), 433-439.

Lilliefors, H. W. (1967). On the kolmogorov-smirnov test for normality with mean and variance unknown. *Journal of the American Statistical Association,* 62(318), 399-402.

Linville, S. E. (2001). *Vocal aging* Singular Thomson Learning.

Littner, M. R. (2007). Mild obstructive sleep apnea syndrome should not be treated. con. *Journal of Clinical Sleep Medicine: JCSM: Official Publication of the American Academy of Sleep Medicine,* 3(3), 263-264.

Medscape. (Aug. 23, 2016, *Should we treat mild obstructive sleep apnea?*

Montazeri, A., Giannouli, E., & Moussavi, Z. (2012). Assessment of obstructive sleep apnea and its severity during wakefulness. *Annals of Biomedical Engineering,* 40(4), 916-924.

Moussavi, Z., Elwali, A., Soltanzadeh, R., MacGregor, C., & Lithgow, B. (2015). Breathing sounds characteristics correlate with structural changes of upper airway due to obstructive sleep apnea. Paper presented at the *Engi-*

40

*neering in Medicine and Biology Society (EMBC),* 2015 37th Annual International Conference of the IEEE, 5956-5959.

Nagappa, M., Liao, P., Wong, J., Auckley, D., Ramachandran, S. K., Memtsoudis, S., . . . Chung, F. (2015). Validation of the STOP-BANG questionnaire as a screening tool for obstructive sleep apnea among different populations: A systematic review and meta-analysis. *PLoS One,* 10(12), e0143697.

Nikias, C. L., & Raghuveer, M. R. (1987). Bispectrum estimation: A digital signal processing framework. *Proceedings of the IEEE,* 75(7), 869-891.

Proakis, J. (2006). DG monolakis-digital signal processing., 911.

ResMed. (2013). *Sleep apnea facts and figures.* ResMed Corp.

Solà-Soler, J., Fiz, J. A., Torres, A., & Jané, R. (2014). Identification of obstructive sleep apnea patients from tracheal breath sound analysis during wakefulness in polysomnographic studies. Paper presented at the *Engineering in Medicine and Biology Society (EMBC),* 2014 36th Annual International Conference of the IEEE, 4232-4235.

Titze, I. (2000). Principles of voice production (national center for voice and speech, iowa city, IA). *Chap,* 6, 149-184.

Torre III, P., & Barlow, J. A. (2009). Age-related changes in acoustic characteristics of adult speech. *Journal of Communication Disorders,* 42(5), 324-333.

Tukey, J. W. (1977). *Exploratory data analysis* Reading, Mass.

Vavougios, G. D., Natsios, G., Pastaka, C., Zarogiannis, S. G., & Gourgoulianis, K. I. (2016). Phenotypes of comorbidity in OSAS patients: Combining categorical principal component analysis with cluster analysis. *Journal of Sleep Research,* 25(1), 31-38.

Young, T., Finn, L., Peppard, P. E., Szklo-Coxe, M., Austin, D., Nieto, F. J., . . . Hla, K. M. (2008). Sleep disordered breathing and mortality: Eighteen-year follow-up of the Wisconsin sleep cohort. *Sleep,* 31(8), 1071-1078.

AwakeOSA—Experiment B

Battiti, R. (1994). Using mutual information for selecting features in supervised neural net learning. *IEEE Transactions on Neural Networks,* 5(4), 537-550.

Brown, G. (2009). A new perspective for information theoretic feature selection. Paper presented at the *Artificial Intelligence and Statistics,* 49-56.

Chatterjee, S., & Hadi, A. S. (1986). Influential observations, high leverage points, and outliers in linear regression. *Statistical Science,* 1(3), 379-393.

Elwali, A., & Moussavi, Z. (2016). Obstructive sleep apnea screening and airway structure characterization during wakefulness using tracheal breathing sounds. *Annals of Biomedical Engineering,* 1-12. breathing sounds. *Scientific Reports,* 9(1), 1-12.

Fleuret, F. (2004). Fast binary feature selection with conditional mutual information. *Journal of Machine Learning Research,* 5(November), 1531-1555.

Peng, H., & Ding, C. (2005). Minimum redundancy and maximum relevance feature selection and recent advances in cancer classification. *Feature Selection for Data Mining,* 52

Spearman, C. (1904). The proof and measurement of association between two things. *American Journal of Psychology,* 15(1), 72-101.

Yang, H., & Moody, J. (1999). Feature selection based on joint mutual information. Paper presented at the *Proceedings of International ICSC Symposium on Advances in Intelligent Data Analysis*, 22-25.

Microphone Coupler

[1] H. Pasterkamp, S. S. Kraman, P. D. DeFrain and G. R. Wodicka, "Measurement of Respiratory Acoustical Signals: Comparison of Sensors," *Chest*, vol. 104, no. 5, pp. 1518-1525, 1993.

[2] A. Yadollahi and Z. Moussavi, "Acoustical Flow Estimation: Review and Validation," *IEEE Magazine in Biomedical Engineering*, vol. 26, no. 1, pp. 56-61, 2007.

[3] G. R. Wodicka, S. S. Kraman, G. M. Zenk and H. Pasterkamp, "Measurement of Respiratory Acoustic Signals: Effect of Microphone Air Cavity Depth," *Chest*, vol. 106, pp. 1140-1144, 1994.

[4] A. Yadollahi, E. Giannouli and Z. Moussavi, "Sleep apnea monitoring and diagnosis based on pulse oximetery and tracheal sound signals," *Medical &biological engineering &computing*, vol. 48, no. 11, pp. 1087-1097, 2010.

[5] A. Yadollahi and Z. Moussavi, "The effect of anthropometric variations on acoustical flow estimation: proposing a novel approach for flow estimation without the need for individual calibration," *IEEE Transactions on Biomedical Engineering*, vol. 58, no. 6, pp. 1663-1670, 2011.

[6] A. Montazeri, E. Giannouli and Z. Moussavi, "Assessment of obstructive sleep apnea and its severity during wakefulness," *Annals of biomedical engineering*, vol. 40, no. 4, pp. 916-924, 2012.

[7] A. Elwali and Z. Moussavi, "A novel diagnostic decision making procedure for screening obstructive sleep apnea using anthropometric information and tracheal breathing sounds during wakefulness," *Scientific Reports (Nature)*, vol. 9, no. 1, pp. 1-12, 2019.

[8] A. Elwali and Z. Moussavi, "Obstructive Sleep Apnea Screening and Airway Structure Characterization During Wakefulness Using Tracheal Breathing Sounds," *Annals of Biomedical Engineering*, vol. 45, no. 3, pp. 839-850, 2017.

[9] S. S. Kraman, H. Pasterkamp, G. R. Wodicka and Y. Oh, "Measurement of respiratory acoustic signals: effect of microphone air cavity width, shape and venting," *Chest*, vol. 108, no. 4, p. 1004-1008, 1995.

The invention claimed is:

1. A method for improving computational analysis of physiological signals to derive a machine-learning obstructive sleep apnea (OSA) screening tool from a heterogeneous initial dataset containing confounding anthropometric variables, said method comprising:

(a) storage, in non-transitory computer readable memory, of an initial dataset that comprises, for each of a plurality of human test subjects from whom respective audio recordings were taken during periods of wakefulness, a respective subject dataset in which there is stored at least:

a known OSA severity parameter of the test subject;

anthropometric data identifying different anthropometric parameters of the test subject; and audio data containing stored audio signals from said respective audio recording of said test subject;

(b) extraction, by said computer, of at least spectral and bi-spectral features from the audio data of the subject datasets;

(c) selection of a training dataset from said initial dataset, and from said training dataset, grouping together the subject datasets from a first high-severity group of said test subjects whose known OSA severity parameters are above a first threshold, and grouping together the subject datasets of a second low-severity group of said test subjects whose known OSA severity parameters are below a second threshold that is lesser than said first threshold;

(d) based on the anthropometric data, division of the subject datasets from each of the high-severity and low-severity groups into a plurality of anthropometrically distinct subsets, among which the subject data sets in each subset share a common confounding anthropometric variable, thereby partitioning the heterogeneous initial dataset for targeted modeling;

(e) derivation, by said computer, of input for a classifier training procedure at least partly by:

(i) for each anthropometrically distinct subset, filtering said extracted spectral and bi-spectral features down to a selected subset of features;

(ii) for each anthropometrically distinct subset, creating a respective pool of predictive models for predicting OSA severity values, of which each predictive model in said pool is based on a different combination of features from the selected subset of features; and (iii) for each anthropometrically distinct subset, evaluating the predictive models of the respective pool against one another to reduce the respective pool down to a reduced subset of the predictive models, by, for each predictive model in the pool: (1) dividing a response variable of the model into a plurality of severity segments; (2) calculating a unique correlation value for each of the plurality of severity segments to account for regional non-linearity; (3) determining an average of the calculated correlation values; and (4) filtering the pool of predictive models to generate the reduced subset based on said average of the calculated correlation values;

(f) using said derived input, training by said computer of a classifier for the purpose of classifying a human patient as either OSA or non-OSA based on a respective patient dataset that contains at least:

anthropometric data identifying different anthropometric parameters of the patient; and at least one of either:

audio data containing stored audio signals from a respective audio recording of said patient during a period of full wakefulness; and/or feature data concerning features already extracted from said audio signals from the respective audio recording of said patient; and (g) storage in the same or another non-transitory computer readable memory:

said trained classifier;

for each anthropometrically distinct subset, identification of a respective feature set, from among said extracted spectral and bi-spectral features, that is to be used for classification of patients whose anthropometric parameters overlap those of the subject datasets of said anthropometrically distinct subset; and statements and instructions executable by one or more computer processors to:

read the anthropometric data of the patient dataset;

match the anthropometric data of the patient dataset to one or more of the anthropometrically distinctive subsets to identify one or more respective feature sets associated therewith;

based on identification of said one or more respective feature sets, select which particular features are required from the audio data or feature data of the patient dataset; and input said particular features to said trained classifier to classify said patients as either OSA or non-OSA.

2. The method of claim 1 wherein division of the response variable in step (e)(iii) is based on real OSA severity values from the subject datasets of the test subjects.

3. The method of claim 2 wherein step (e)(iii) further comprises, for each of said predictive models in each pool:

calculating average OSA severity values for the first set of different OSA severity groups;

determining whether said average OSA severity values increase or decrease in matching sequence to said first set of different OSA severity groups; and removing from said pool any predictive model whose average OSA severity values do not increase or decrease in matching sequence to said first set of different OSA severity groups.

4. The method of claim 3 wherein said average OSA severity values are calculated averages of predicted OSA severity values from the predictive model.

5. The method of claim 4 wherein step (e)(iii) further comprises, for each of said predictive models in each pool:

dividing datapoints of each of said predictive models in said pool into a second set of different OSA severity groups based on the predicted OSA severity values from the predictive model;

calculating average real OSA severity values for the second set of different OSA severity groups;

determining whether said average real OSA severity values increase or decrease in matching sequence to said second set of different OSA severity groups; and removing from said pool any predictive model whose average real OSA severity values do not increase or decrease in matching sequence to said second set of different OSA severity groups.

6. The method of claim 5 wherein step (e)(iii) further comprises:

for each predictive model in each pool, calculating an overlap percentage between adjacent OSA severity groups in both the first and second sets of different OSA severity groups;

for each predictive model in each pool, calculating an average of the overlap percentages of said predictive model for both the first and second sets of different OSA severity groups.

7. The method of claim 6 wherein step (e)(iii) further comprises:

for each predictive model in each pool, calculating an overall average of the average overlap percentages from both the first and second sets of different OSA severity groups; and filtering each pool down to said reduced subset of the predictive models therein based on which of said predictive models have a lesser overall average overlap percentage than other models from said pool.

8. The method of claim 2 wherein step (e)(iii) further comprises, for each predictive model in each pool, calculating an overlap percentage between adjacent OSA severity groups in each set of different OSA severity groups.

9. The method of claim 8 wherein step (e)(iii) further comprises, for each set of different OSA severity groups for each predictive model in each pool, calculating an average of the overlap percentages of said predictive model.

10. The method of claim 9 wherein step (e)(iii) further comprises, using said average of the overlap percentages of each predictive model, filtering each pool down to said subset of the predictive models therein based on which of said predictive models have a lesser average overlap between said adjacent OSA severity groups than other models from said pool.

11. The method of claim 1 wherein step (c) comprises also selecting a blind dataset from said initial dataset, and step (e)(iii) further comprises, from each pool, running each predictive model from said pool using the subject datasets from the blind dataset to calculate estimated OSA severity values for said blind dataset, and assessing an accuracy of said estimated OSA severity values against real OSA severity values from said blind dataset.

12. The method of claim 11 wherein step (f) comprises, for each predictive model in each pool, at least one training procedure having a classifier training step and a classifier testing step, of which the classifier training step comprises running the classifier with model-predicted OSA severity values from a subset of the training dataset, and the classifier testing step comprises rerunning of the classifier with model-predicted OSA severity values from the same or a different subset of the training dataset, and evaluating classification results from said rerunning off the classifier against real OSA severity values from said same or different subset of the training dataset.

13. The method of claim 1 wherein step (c) comprises also selecting a blind dataset from said initial dataset, and step (f) comprises, for each predictive model in the reduced subset of the predictive models, at least one training procedure having a classifier training step and a classifier validation step, of which the classifier training step comprises running the classifier with model-predicted OSA severity values from a subset of the training dataset, and the classifier validation step comprises rerunning the classifier with model-predicted OSA severity values from the same or a different subset of the training dataset, and comparing classification results from said rerunning of the classifier against real OSA severity values from said same or different subset of the training dataset to evaluate performance of the predictive model.

14. A method of performing an obstructive sleep apnea (OSA) screening test on a patient, said method comprising:

(a) obtaining one or more computer readable media on which there is stored:

a trained classifier derived in the manner recited in at least steps (a) through (f) of claim 1;

for said patient, a patient dataset of the type recited in step (f) of claim 1; and statements and instructions executable by one or more computer processors;

(b) through execution of said statements and instructions by said one or more computer processors:

(i) reading the anthropometric data of said patient dataset;

(ii) running, multiple times, a trained classifier derived in the manner recited in at least steps (a) through (f) of claim 1, each time starting with input composed of or derived from a different feature combination, comprised of at least spectral and bi-spectral features, particularly selected or derived from the patient dataset for a different anthropometric parameter read from the anthropometric data of said patient dataset, and for each run of said trained classifier, deriving therefrom a respective classification result classifying the patient as either OSA or non-OSA;

(iii) based on the classification results from step (b) (ii), deriving a final classification result for the patient; and (iv) storing or displaying said final classification.

15. Non-transitory computer readable memory having stored thereon statements and instructions executable by one or more processors to, when executed, perform at least step (b) of claim 14.

16. The method of claim 14 comprising:

prior to step (a), recording tracheal breathing sounds of said patient during said period of wakefulness, thereby obtaining said respective audio recording of said patient, and digitally storing the audio data containing the stored audio signals from said respective audio recording; and after step (g), diagnosing said patient as having OSA based on the classification from the trained classifier.

17. Non-transitory computer readable memory having stored thereon executable statements and instructions configured to, when executed by the one or more processors, perform at least steps (e) and (f) of claim 1.

18. The method of claim 1 wherein a total quantity of predictive models created in step (e) comprises at least 2,925 predictive models.

19. The method of claim 1 wherein a total quantity of predictive models created in step (e) comprises at least 17,550 predictive models.

20. The method of claim 1 wherein a total quantity of predictive models created in step (e) comprises at least 80,730 predictive models.

* * * * *